(12) United States Patent
Denmeade et al.

(10) Patent No.: US 7,053,042 B1
(45) Date of Patent: May 30, 2006

(54) ACTIVATION OF PEPTIDE PRODRUGS BY HK2

(75) Inventors: Samuel R. Denmeade, Ellicott City, MD (US); John T. Isaacs, Pheonix, MD (US); Hans Lilja, Gesailens gata 17, S-239 35 Skanor (SE)

(73) Assignees: Samuel Denmeade, Ellicott City, MD (US); John Tod Isaacs, Pheonix, MD (US); Hans Lilja (SE)

( * ) Notice: Subject to any disclaimer, the term of this patent is extended or adjusted under 35 U.S.C. 154(b) by 890 days.

(21) Appl. No.: 09/627,600

(22) Filed: Jul. 28, 2000

Related U.S. Application Data

(60) Provisional application No. 60/146,316, filed on Jul. 29, 1999.

(51) Int. Cl.
*A61K 35/00* (2006.01)
*C07K 14/81* (2006.01)
*C07K 19/00* (2006.01)

(52) U.S. Cl. ............... 514/2; 530/378.2; 530/300; 530/350; 424/94.1; 424/94.6; 424/9.1; 424/178.1; 435/195

(58) Field of Classification Search ............ 514/2; 530/378.3, 300, 350; 424/9.1, 178, 94.1, 424/946; 435/195
See application file for complete search history.

(56) References Cited

U.S. PATENT DOCUMENTS

| | | | |
|---|---|---|---|
| 5,599,686 A | 2/1997 | DeFeo-Jones et al. | ........ 435/23 |
| 5,603,933 A | 2/1997 | Dwyer, IV et al. | ...... 424/185.1 |
| 5,618,790 A | 4/1997 | Kennedy et al. | ............ 514/12 |
| 5,741,821 A | 4/1998 | Roufogalis et al. | ........ 514/734 |
| 5,866,679 A | 2/1999 | DeFeo-Jones et al. | ...... 530/322 |
| 5,905,089 A | 5/1999 | Hwang et al. | ............ 514/468 |
| 5,955,431 A | 9/1999 | Stevens et al. | ............. 514/17 |
| 6,545,131 B1 * | 4/2003 | Isaacs et al. | ............. 530/391.7 |

FOREIGN PATENT DOCUMENTS

| | | |
|---|---|---|
| JP | 3-15886 | 1/1991 |
| WO | WO 97/28272 | 8/1997 |
| WO | WO 98/20135 | 5/1998 |
| WO | WO 99/40930 | 8/1999 |

OTHER PUBLICATIONS

Treiman et al., "A tool coming of age: thapsigargin as an inhibitor of sarco-endoplasmic reticulum $Ca^{2+}$- ATPases", TiPS, Apr. 1998, vol. 19, pp 131-135.
Anderen et al., "$Ca^{2+}$-ATPase Inhibitory Activity Of a Locked Analogue of Thapsigargin",*Bioorganic & Medicinal Chemistry Letters*, vol. 4, No. 5, pp 657-660, 1994.
Nielsen et al., "Structure-Activity Relationships of Analogues of Thapsigargin Modified at 0-11 and 0-12", *J. Med. Chem.*, 1995, vol. 38, pp 272-276.
Bourgeois et al., "Serpin-derived Peptide Substrates . . . Kallikreins hK1 and hK2", *The Journal of Biological Chemistry*, vol. 272, No. 47, Issue of Nov. 21, pp. 29590-29595, 1997.
Denmeade et al., "Specific and Efficient Peptide . . . of Prostate-specific Antigen", *Cancer Research*, vol. 57, pp. 4924-4930, Nov. 1,1997.
Coombs et al., Substrate specificity of prostate-specific antigen (PSA), *Chemistry & Biology*, vol. 5, No. 9, Sep. 1998, pp 475-488.
Brillard-Bourdet et al., "Substrate specificity . . . extended interaction site", *BBA*, vol. 1246, No. 1, Jan. 5, 1995, pp. 47-52.
Devi, "Consensus sequence . . . peptide precursors . . . sites", *FEBS LETTERS*, vol. 280, No. 2, Mar. 25, 1991, pp 189-194.
Nakayama et al., "Consensus Sequence for Precursor Processing at Mono-arginyl Sites", *The Journal of Biological Chemistry*, vol. 267, No. 23, Issue of Aug. 15, pp. 16335-16340, 1992.

(Continued)

*Primary Examiner*—Karen Cochrane Carlson
*Assistant Examiner*—Samuel W. Liu
(74) *Attorney, Agent, or Firm*—Peter F. Corless; Edwards & Angell, LLP

(57) ABSTRACT

The invention provides novel peptide prodrugs that contain cleavage sites specifically cleaved by human kallikrein 2 (hK2). These prodrugs are useful for substantially inhibiting the non-specific toxicity of a variety of therapeutic drugs. Upon cleavage of the prodrug by hK2, the therapeutic drugs are activated and exert their toxicity. Methods for treating cell proliferative disorders are also featured in the invention.

40 Claims, 1 Drawing Sheet

OTHER PUBLICATIONS

Dube, "La Kallicreine HK2 Peut-Elle Favoriser La Progression Des Tumeurs Cancereuses De La Prostate", Science and Medicine, 14(1):111-113 (1998).

Bougeois et al., Serpin-derived peptide substrates for investigating the substrate specificity of human tissue kallikrein hk1 and hk2, Journal of Biological Chemistry, 272(47):29590-29595 (1997).

Lovgren et al., "Enzymatic action of human glandular kallikrein 2 (hK2) : Substrate specificity and regulation by Zn2+ and extracellular protease inhibitors", European Journal of Biochemistry, 262 (3) : 781-789 (1999).

Mikolajczyk et al., "Human glandular kallikrein, hK2, shows arginine-restricted specificity and forms complexes with plasma protease inhibitors", Prostate, 34 (1) :44-50 (1998).

Denmeade et al., "Enzymatic Activation of Prodrugs by Prostate-Specific Antigen: Targeted Thereapy for Metastatic Prostate Cancer", Cancer Journal from Scientific American, 4, Suppl. 1:S15-S21 (1998).

Denmeade et al., "Enzymatic activation of a doxorubicin-peptide prodrug by prostate-specific antigen", Cancer Research, 58:2537-2540 (1994).

James et al., "Basic Amino Acids Predominate in the Sequential Autoantigenic Determinants of the Small Juclear 70K Ribonucleoprotein", Scandinavian Journal of Immunology, 39 (6) :557-566 (1994).

Pimenta et al., "Specificity of human tissue kallikrein towards substrates containing Phe-Phe pair of amino acids", Biochemical Journal, 339 (2) :473-479 (1999).

* cited by examiner

| | P8 | P7 | P6 | P5 | P4 | P3 | P2 | P1 | P-1 | P-2 | P-3 |
|---|---|---|---|---|---|---|---|---|---|---|---|
| Semenogelin I | | | | | | | | | | | |
| 107 / 114 / 117 | — His | Lys | Gly | Gly | Lys | Ala | His | Arg ▼ | Gly | Thr | Gln — |
| 267 / 274 / 277 | — Ser | Ser | Ser | Tyr | Glu | Glu | Arg | Arg | Leu | His | Tyr — |
| 327 / 334 / 377 | — Ser | Ser | Ser | Tyr | Glu | Glu | Arg | Arg | Leu | His | Tyr — |
| 342 / 349 / 352 | — Val | Gln | Lys | Asp | Val | Ser | Gln | Arg | Ser | Ile | Tyr — |
| Semenogelin II | | | | | | | | | | | |
| 94 / 101 / 104 | — Asp | Lys | Ser | Lys | Gly | His | Phe | His ▼ | Met | Ile | Val — |
| 135 / 142 / 145 | — Gln | Cys | Ser | Asn | Thr | Glu | Lys | Arg | Leu | Trp | Val — |
| 215 / 222 / 225 | — Leu | His | Pro | Ala | His | Gln | Asp | Arg | Leu | Gln | His — |
| 262 / 269 / 272 | — Lys | Ile | Ser | Tyr | Pro | Ser | Ser | Arg | Thr | Glu | Glu — |
| 361 / 368 / 371 | — Gly | Lys | Ser | Gln | Asn | Gln | Val | Arg | Ile | Pro | Ser — |
| 447 / 454 / 457 | — Ser | Ser | Ser | Tyr | Glu | Glu | Arg | Arg | Leu | Asn | Tyr — |
| 515 / 522 / 525 | — Leu | Ser | His | Glu | Gln | Lys | Gly | Arg | Tyr | Lys | Gln — |

SEQUENCE LISTING

<160> NUMBER OF SEQ ID NOS: 135

<210> SEQ ID NO 1
<211> LENGTH: 11
<212> TYPE: PRT
<213> ORGANISM: Homo sapiens

<400> SEQUENCE: 1

His Lys Gly Gly Lys Ala His Arg Gly Thr Gln
 1               5                  10

<210> SEQ ID NO 2
<211> LENGTH: 11
<212> TYPE: PRT
<213> ORGANISM: Homo sapiens

<400> SEQUENCE: 2

Ser Ser Ser Tyr Glu Glu Arg Arg Leu His Tyr
 1               5                  10

<210> SEQ ID NO 3
<211> LENGTH: 11
<212> TYPE: PRT
<213> ORGANISM: Homo sapiens

<400> SEQUENCE: 3

Ser Ser Ser Tyr Glu Glu Arg Arg Leu His Tyr
 1               5                  10

<210> SEQ ID NO 4
<211> LENGTH: 11
<212> TYPE: PRT
<213> ORGANISM: Homo sapiens

<400> SEQUENCE: 4

Val Gln Lys Asp Val Ser Gln Arg Ser Ile Tyr
 1               5                  10

<210> SEQ ID NO 5
<211> LENGTH: 11
<212> TYPE: PRT
<213> ORGANISM: Homo sapiens

<400> SEQUENCE: 5

Asp Lys Ser Lys Gly His Phe His Met Ile Val
 1               5                  10

<210> SEQ ID NO 6
<211> LENGTH: 11
<212> TYPE: PRT
<213> ORGANISM: Homo sapiens

<400> SEQUENCE: 6

Gln Cys Ser Asn Thr Glu Lys Arg Leu Trp Val
 1               5                  10

<210> SEQ ID NO 7
<211> LENGTH: 11

```
<212> TYPE: PRT
<213> ORGANISM: Homo sapiens

<400> SEQUENCE: 7

Leu His Pro Ala His Gln Asp Arg Leu Gln His
  1               5                  10

<210> SEQ ID NO 8
<211> LENGTH: 11
<212> TYPE: PRT
<213> ORGANISM: Homo sapiens

<400> SEQUENCE: 8

Lys Ile Ser Tyr Pro Ser Ser Arg Thr Glu Glu
  1               5                  10

<210> SEQ ID NO 9
<211> LENGTH: 11
<212> TYPE: PRT
<213> ORGANISM: Homo sapiens

<400> SEQUENCE: 9

Gly Lys Ser Gln Asn Gln Val Arg Ile Pro Ser
  1               5                  10

<210> SEQ ID NO 10
<211> LENGTH: 11
<212> TYPE: PRT
<213> ORGANISM: Homo sapiens

<400> SEQUENCE: 10

Ser Ser Ser Tyr Glu Glu Arg Arg Leu Asn Tyr
  1               5                  10

<210> SEQ ID NO 11
<211> LENGTH: 11
<212> TYPE: PRT
<213> ORGANISM: Homo sapiens

<400> SEQUENCE: 11

Leu Ser His Glu Gln Lys Gly Arg Tyr Lys Gln
  1               5                  10

<210> SEQ ID NO 12
<211> LENGTH: 3
<212> TYPE: PRT
<213> ORGANISM: Homo sapiens

<400> SEQUENCE: 12

Lys Arg Arg
  1

<210> SEQ ID NO 13
<211> LENGTH: 3
<212> TYPE: PRT
<213> ORGANISM: Homo sapiens

<400> SEQUENCE: 13

Ser Arg Arg
  1

<210> SEQ ID NO 14
<211> LENGTH: 3
<212> TYPE: PRT
<213> ORGANISM: Homo sapiens
```

```
<400> SEQUENCE: 14

Ala Arg Arg
1

<210> SEQ ID NO 15
<211> LENGTH: 3
<212> TYPE: PRT
<213> ORGANISM: Homo sapiens

<400> SEQUENCE: 15

His Arg Arg
1

<210> SEQ ID NO 16
<211> LENGTH: 3
<212> TYPE: PRT
<213> ORGANISM: Homo sapiens

<400> SEQUENCE: 16

Gln Arg Arg
1

<210> SEQ ID NO 17
<211> LENGTH: 3
<212> TYPE: PRT
<213> ORGANISM: Homo sapiens

<400> SEQUENCE: 17

Ala Phe Arg
1

<210> SEQ ID NO 18
<211> LENGTH: 3
<212> TYPE: PRT
<213> ORGANISM: Homo sapiens

<400> SEQUENCE: 18

Ala Gln Arg
1

<210> SEQ ID NO 19
<211> LENGTH: 3
<212> TYPE: PRT
<213> ORGANISM: Homo sapiens

<400> SEQUENCE: 19

Ala Lys Arg
1

<210> SEQ ID NO 20
<211> LENGTH: 3
<212> TYPE: PRT
<213> ORGANISM: Homo sapiens

<400> SEQUENCE: 20

Ala Arg Lys
1

<210> SEQ ID NO 21
<211> LENGTH: 3
<212> TYPE: PRT
<213> ORGANISM: Homo sapiens

<400> SEQUENCE: 21
```

Ala His Arg
1

<210> SEQ ID NO 22
<211> LENGTH: 4
<212> TYPE: PRT
<213> ORGANISM: Homo sapiens

<400> SEQUENCE: 22

Gln Lys Arg Arg
1

<210> SEQ ID NO 23
<211> LENGTH: 4
<212> TYPE: PRT
<213> ORGANISM: Homo sapiens

<400> SEQUENCE: 23

Lys Ser Arg Arg
1

<210> SEQ ID NO 24
<211> LENGTH: 4
<212> TYPE: PRT
<213> ORGANISM: Homo sapiens

<400> SEQUENCE: 24

Ala Lys Arg Arg
1

<210> SEQ ID NO 25
<211> LENGTH: 4
<212> TYPE: PRT
<213> ORGANISM: Homo sapiens

<400> SEQUENCE: 25

Lys Lys Arg Arg
1

<210> SEQ ID NO 26
<211> LENGTH: 4
<212> TYPE: PRT
<213> ORGANISM: Homo sapiens

<400> SEQUENCE: 26

His Lys Arg Arg
1

<210> SEQ ID NO 27
<211> LENGTH: 4
<212> TYPE: PRT
<213> ORGANISM: Homo sapiens

<400> SEQUENCE: 27

Lys Ala Phe Arg
1

<210> SEQ ID NO 28
<211> LENGTH: 4
<212> TYPE: PRT
<213> ORGANISM: Homo sapiens

<400> SEQUENCE: 28

Lys Ala Gln Arg

```
<210> SEQ ID NO 29
<211> LENGTH: 4
<212> TYPE: PRT
<213> ORGANISM: Homo sapiens

<400> SEQUENCE: 29

Lys Ala Lys Arg
1

<210> SEQ ID NO 30
<211> LENGTH: 4
<212> TYPE: PRT
<213> ORGANISM: Homo sapiens

<400> SEQUENCE: 30

Lys Ala Arg Lys
1

<210> SEQ ID NO 31
<211> LENGTH: 4
<212> TYPE: PRT
<213> ORGANISM: Homo sapiens

<400> SEQUENCE: 31

Lys Ala His Arg
1

<210> SEQ ID NO 32
<211> LENGTH: 4
<212> TYPE: PRT
<213> ORGANISM: Homo sapiens

<400> SEQUENCE: 32

Lys Arg Arg Leu
1

<210> SEQ ID NO 33
<211> LENGTH: 4
<212> TYPE: PRT
<213> ORGANISM: Homo sapiens

<400> SEQUENCE: 33

Ser Arg Arg Leu
1

<210> SEQ ID NO 34
<211> LENGTH: 4
<212> TYPE: PRT
<213> ORGANISM: Homo sapiens

<400> SEQUENCE: 34

Ala Arg Arg Leu
1

<210> SEQ ID NO 35
<211> LENGTH: 4
<212> TYPE: PRT
<213> ORGANISM: Homo sapiens

<400> SEQUENCE: 35

Ala Arg Arg Ser
1
```

```
<210> SEQ ID NO 36
<211> LENGTH: 4
<212> TYPE: PRT
<213> ORGANISM: Homo sapiens

<400> SEQUENCE: 36

His Arg Arg Ala
 1

<210> SEQ ID NO 37
<211> LENGTH: 4
<212> TYPE: PRT
<213> ORGANISM: Homo sapiens

<400> SEQUENCE: 37

Gln Arg Arg Leu
 1

<210> SEQ ID NO 38
<211> LENGTH: 4
<212> TYPE: PRT
<213> ORGANISM: Homo sapiens

<400> SEQUENCE: 38

Ala Phe Arg Leu
 1

<210> SEQ ID NO 39
<211> LENGTH: 4
<212> TYPE: PRT
<213> ORGANISM: Homo sapiens

<400> SEQUENCE: 39

Ala Gln Arg Leu
 1

<210> SEQ ID NO 40
<211> LENGTH: 4
<212> TYPE: PRT
<213> ORGANISM: Homo sapiens

<400> SEQUENCE: 40

Ala Lys Arg Leu
 1

<210> SEQ ID NO 41
<211> LENGTH: 4
<212> TYPE: PRT
<213> ORGANISM: Homo sapiens

<400> SEQUENCE: 41

Ala Arg Lys Leu
 1

<210> SEQ ID NO 42
<211> LENGTH: 4
<212> TYPE: PRT
<213> ORGANISM: Homo sapiens

<400> SEQUENCE: 42

Ala His Arg Leu
 1

<210> SEQ ID NO 43
```

```
<211> LENGTH: 7
<212> TYPE: PRT
<213> ORGANISM: Homo sapiens

<400> SEQUENCE: 43

His Ala Gln Lys Arg Arg Leu
 1               5

<210> SEQ ID NO 44
<211> LENGTH: 7
<212> TYPE: PRT
<213> ORGANISM: Homo sapiens

<400> SEQUENCE: 44

Gly Gly Lys Ser Arg Arg Leu
 1               5

<210> SEQ ID NO 45
<211> LENGTH: 7
<212> TYPE: PRT
<213> ORGANISM: Homo sapiens

<400> SEQUENCE: 45

His Glu Gln Lys Arg Arg Leu
 1               5

<210> SEQ ID NO 46
<211> LENGTH: 7
<212> TYPE: PRT
<213> ORGANISM: Homo sapiens

<400> SEQUENCE: 46

His Glu Ala Lys Arg Arg Leu
 1               5

<210> SEQ ID NO 47
<211> LENGTH: 7
<212> TYPE: PRT
<213> ORGANISM: Homo sapiens

<400> SEQUENCE: 47

Gly Gly Gln Lys Arg Arg Leu
 1               5

<210> SEQ ID NO 48
<211> LENGTH: 7
<212> TYPE: PRT
<213> ORGANISM: Homo sapiens

<400> SEQUENCE: 48

His Glu Gln Lys Arg Arg Ala
 1               5

<210> SEQ ID NO 49
<211> LENGTH: 7
<212> TYPE: PRT
<213> ORGANISM: Homo sapiens

<400> SEQUENCE: 49

Gly Gly Ala Lys Arg Arg Leu
 1               5

<210> SEQ ID NO 50
<211> LENGTH: 7
<212> TYPE: PRT
```

```
<213> ORGANISM: Homo sapiens

<400> SEQUENCE: 50

His Glu Gln Lys Arg Arg Ser
 1               5

<210> SEQ ID NO 51
<211> LENGTH: 7
<212> TYPE: PRT
<213> ORGANISM: Homo sapiens

<400> SEQUENCE: 51

Gly Gly Lys Lys Arg Arg Leu
 1               5

<210> SEQ ID NO 52
<211> LENGTH: 7
<212> TYPE: PRT
<213> ORGANISM: Homo sapiens

<400> SEQUENCE: 52

Gly Gly His Lys Arg Arg Leu
 1               5

<210> SEQ ID NO 53
<211> LENGTH: 5
<212> TYPE: PRT
<213> ORGANISM: Homo sapiens
<220> FEATURE:
<221> NAME/KEY: VARIANT
<222> LOCATION: 1
<223> OTHER INFORMATION: Xaa = Boc (t-butoxy carbonyl)
<220> FEATURE:
<221> NAME/KEY: VARIANT
<222> LOCATION: 5
<223> OTHER INFORMATION: Xaa = AMC (aminomethylcoumarin)

<400> SEQUENCE: 53

Xaa Phe Ser Arg Xaa
 1               5

<210> SEQ ID NO 54
<211> LENGTH: 5
<212> TYPE: PRT
<213> ORGANISM: Homo sapiens
<220> FEATURE:
<221> NAME/KEY: VARIANT
<222> LOCATION: 1
<223> OTHER INFORMATION: Xaa = Boc (t-butoxy carbonyl)
<220> FEATURE:
<221> NAME/KEY: VARIANT
<222> LOCATION: 5
<223> OTHER INFORMATION: Xaa = AMC (aminomethylcoumarin)

<400> SEQUENCE: 54

Xaa Gln Gly Arg Xaa
 1               5

<210> SEQ ID NO 55
<211> LENGTH: 5
<212> TYPE: PRT
<213> ORGANISM: Homo sapiens
<220> FEATURE:
<221> NAME/KEY: VARIANT
<222> LOCATION: 1
<223> OTHER INFORMATION: Xaa = H (hydrogen)
<220> FEATURE:
<221> NAME/KEY: VARIANT
<222> LOCATION: 5
```

```
<223> OTHER INFORMATION: Xaa = AMC (aminomethylcoumarin)

<400> SEQUENCE: 55

Xaa Pro Phe Arg Xaa
 1               5

<210> SEQ ID NO 56
<211> LENGTH: 5
<212> TYPE: PRT
<213> ORGANISM: Homo sapiens
<220> FEATURE:
<221> NAME/KEY: VARIANT
<222> LOCATION: 1
<223> OTHER INFORMATION: Xaa = Boc (t-butoxy carbonyl)
<220> FEATURE:
<221> NAME/KEY: VARIANT
<222> LOCATION: 5
<223> OTHER INFORMATION: Xaa = AMC (aminomethylcoumarin)

<400> SEQUENCE: 56

Xaa Val Pro Arg Xaa
 1               5

<210> SEQ ID NO 57
<211> LENGTH: 5
<212> TYPE: PRT
<213> ORGANISM: Homo sapiens
<220> FEATURE:
<221> NAME/KEY: VARIANT
<222> LOCATION: 1
<223> OTHER INFORMATION: Xaa = H-D (free amine without protecting group)
<220> FEATURE:
<221> NAME/KEY: VARIANT
<222> LOCATION: 5
<223> OTHER INFORMATION: Xaa = AMC (aminomethylcoumarin)

<400> SEQUENCE: 57

Xaa Val Leu Lys Xaa
 1               5

<210> SEQ ID NO 58
<211> LENGTH: 5
<212> TYPE: PRT
<213> ORGANISM: Homo sapiens
<220> FEATURE:
<221> NAME/KEY: VARIANT
<222> LOCATION: 1
<223> OTHER INFORMATION: Xaa = Tos (4-Toluenesulphonyl)
<220> FEATURE:
<221> NAME/KEY: VARIANT
<222> LOCATION: 5
<223> OTHER INFORMATION: Xaa = AMC (aminomethylcoumarin)

<400> SEQUENCE: 58

Xaa Gly Pro Arg Xaa
 1               5

<210> SEQ ID NO 59
<211> LENGTH: 5
<212> TYPE: PRT
<213> ORGANISM: Homo sapiens
<220> FEATURE:
<221> NAME/KEY: VARIANT
<222> LOCATION: 1
<223> OTHER INFORMATION: Xaa = Tos (4-Toluenesulphonyl)
<220> FEATURE:
<221> NAME/KEY: VARIANT
<222> LOCATION: 5
<223> OTHER INFORMATION: Xaa = AMC (aminomethylcoumarin)

<400> SEQUENCE: 59
```

```
Xaa Gly Pro Lys Xaa
 1               5

<210> SEQ ID NO 60
<211> LENGTH: 5
<212> TYPE: PRT
<213> ORGANISM: Homo sapiens
<220> FEATURE:
<221> NAME/KEY: VARIANT
<222> LOCATION: 1
<223> OTHER INFORMATION: Xaa = Z (carbobenzyloxy)
<220> FEATURE:
<221> NAME/KEY: VARIANT
<222> LOCATION: 5
<223> OTHER INFORMATION: Xaa = AMC (aminomethylcoumarin)

<400> SEQUENCE: 60

Xaa Leu Leu Arg Xaa
 1               5

<210> SEQ ID NO 61
<211> LENGTH: 5
<212> TYPE: PRT
<213> ORGANISM: Homo sapiens
<220> FEATURE:
<221> NAME/KEY: VARIANT
<222> LOCATION: 1
<223> OTHER INFORMATION: Xaa = Z (carbobenzyloxy)
<220> FEATURE:
<221> NAME/KEY: VARIANT
<222> LOCATION: 5
<223> OTHER INFORMATION: Xaa = AMC (aminomethylcoumarin)

<400> SEQUENCE: 61

Xaa Val Val Arg Xaa
 1               5

<210> SEQ ID NO 62
<211> LENGTH: 5
<212> TYPE: PRT
<213> ORGANISM: Homo sapiens
<220> FEATURE:
<221> NAME/KEY: VARIANT
<222> LOCATION: 1
<223> OTHER INFORMATION: Xaa = Z (carbobenzyloxy)
<220> FEATURE:
<221> NAME/KEY: VARIANT
<222> LOCATION: 5
<223> OTHER INFORMATION: Xaa = AMC (aminomethylcoumarin)

<400> SEQUENCE: 62

Xaa Ala Arg Arg Xaa
 1               5

<210> SEQ ID NO 63
<211> LENGTH: 6
<212> TYPE: PRT
<213> ORGANISM: Homo sapiens
<220> FEATURE:
<221> NAME/KEY: VARIANT
<222> LOCATION: 1
<223> OTHER INFORMATION: Xaa = H (hydrogen)
<220> FEATURE:
<221> NAME/KEY: VARIANT
<222> LOCATION: 5
<223> OTHER INFORMATION: Xaa = AMC (aminomethylcoumarin)

<400> SEQUENCE: 63

Xaa Arg Gln Arg Arg Xaa
 1               5
```

```
<210> SEQ ID NO 64
<211> LENGTH: 10
<212> TYPE: PRT
<213> ORGANISM: Homo sapiens
<220> FEATURE:
<221> NAME/KEY: VARIANT
<222> LOCATION: 1
<223> OTHER INFORMATION: Xaa = Mu (morphourea)
<220> FEATURE:
<221> NAME/KEY: VARIANT
<222> LOCATION: 10
<223> OTHER INFORMATION: Xaa = AMC (aminomethylcoumarin)

<400> SEQUENCE: 64

Xaa Ala Pro Val Leu Ile Leu Ser Arg Xaa
 1               5                  10

<210> SEQ ID NO 65
<211> LENGTH: 9
<212> TYPE: PRT
<213> ORGANISM: Homo sapiens
<220> FEATURE:
<221> NAME/KEY: VARIANT
<222> LOCATION: 1
<223> OTHER INFORMATION: Xaa = Mu (morphourea)
<220> FEATURE:
<221> NAME/KEY: VARIANT
<222> LOCATION: 9
<223> OTHER INFORMATION: Xaa = AMC (aminomethylcoumarin)

<400> SEQUENCE: 65

Xaa Val Pro Leu Ile Gln Ser Arg Xaa
 1               5

<210> SEQ ID NO 66
<211> LENGTH: 8
<212> TYPE: PRT
<213> ORGANISM: Homo sapiens

<400> SEQUENCE: 66

Gly His Glu Gln Lys Arg Arg Leu
 1               5

<210> SEQ ID NO 67
<211> LENGTH: 8
<212> TYPE: PRT
<213> ORGANISM: Homo sapiens

<400> SEQUENCE: 67

Gly Gly Gly Lys Ala Arg Arg Leu
 1               5

<210> SEQ ID NO 68
<211> LENGTH: 8
<212> TYPE: PRT
<213> ORGANISM: Homo sapiens

<400> SEQUENCE: 68

Gly Gly Gly Lys Ala His Arg Leu
 1               5

<210> SEQ ID NO 69
<211> LENGTH: 8
<212> TYPE: PRT
<213> ORGANISM: Homo sapiens

<400> SEQUENCE: 69
```

Gly Pro Ala His Gln Arg Arg Leu
1               5

<210> SEQ ID NO 70
<211> LENGTH: 8
<212> TYPE: PRT
<213> ORGANISM: Homo sapiens

<400> SEQUENCE: 70

Gly Ser Lys Gly His Phe Arg Leu
1               5

<210> SEQ ID NO 71
<211> LENGTH: 8
<212> TYPE: PRT
<213> ORGANISM: Homo sapiens

<400> SEQUENCE: 71

Gly Ser Lys Gly His Arg Arg Leu
1               5

<210> SEQ ID NO 72
<211> LENGTH: 8
<212> TYPE: PRT
<213> ORGANISM: Homo sapiens

<400> SEQUENCE: 72

Gly Lys Asp Val Ser Arg Arg Leu
1               5

<210> SEQ ID NO 73
<211> LENGTH: 8
<212> TYPE: PRT
<213> ORGANISM: Homo sapiens

<400> SEQUENCE: 73

Gly Ser Gln Asn Gln Arg Arg Leu
1               5

<210> SEQ ID NO 74
<211> LENGTH: 8
<212> TYPE: PRT
<213> ORGANISM: Homo sapiens

<400> SEQUENCE: 74

Gly Ser Tyr Pro Ser Arg Arg Leu
1               5

<210> SEQ ID NO 75
<211> LENGTH: 8
<212> TYPE: PRT
<213> ORGANISM: Homo sapiens

<400> SEQUENCE: 75

Gly Ser Tyr Pro Ser Ser Arg Leu
1               5

<210> SEQ ID NO 76
<211> LENGTH: 8
<212> TYPE: PRT
<213> ORGANISM: Homo sapiens

<400> SEQUENCE: 76

Gly His Glu Gln Lys Gly Arg Leu

```
<210> SEQ ID NO 77
<211> LENGTH: 8
<212> TYPE: PRT
<213> ORGANISM: Homo sapiens

<400> SEQUENCE: 77

Gly Ser Asn Thr Glu Arg Arg Leu
 1               5

<210> SEQ ID NO 78
<211> LENGTH: 8
<212> TYPE: PRT
<213> ORGANISM: Homo sapiens

<400> SEQUENCE: 78

Gly Ser Tyr Glu Glu Arg Arg Leu
 1               5

<210> SEQ ID NO 79
<211> LENGTH: 8
<212> TYPE: PRT
<213> ORGANISM: Homo sapiens

<400> SEQUENCE: 79

Gly Lys Asp Val Ser Gly Arg Leu
 1               5

<210> SEQ ID NO 80
<211> LENGTH: 8
<212> TYPE: PRT
<213> ORGANISM: Homo sapiens

<400> SEQUENCE: 80

Gly Ser Asn Thr Glu Lys Arg Leu
 1               5

<210> SEQ ID NO 81
<211> LENGTH: 8
<212> TYPE: PRT
<213> ORGANISM: Homo sapiens

<400> SEQUENCE: 81

Gly Ser Lys Gly His Phe His Leu
 1               5

<210> SEQ ID NO 82
<211> LENGTH: 8
<212> TYPE: PRT
<213> ORGANISM: Homo sapiens

<400> SEQUENCE: 82

Gly Ser Gln Asn Gln Val Arg Leu
 1               5

<210> SEQ ID NO 83
<211> LENGTH: 8
<212> TYPE: PRT
<213> ORGANISM: Homo sapiens

<400> SEQUENCE: 83

Gly Pro Leu Ile Leu Ser Arg Leu
 1               5
```

```
<210> SEQ ID NO 84
<211> LENGTH: 8
<212> TYPE: PRT
<213> ORGANISM: Homo sapiens

<400> SEQUENCE: 84

Gly Ser Tyr Glu Glu Arg His Leu
1               5

<210> SEQ ID NO 85
<211> LENGTH: 8
<212> TYPE: PRT
<213> ORGANISM: Homo sapiens

<400> SEQUENCE: 85

Gly Lys Asp Val Ser Gly His Leu
1               5

<210> SEQ ID NO 86
<211> LENGTH: 8
<212> TYPE: PRT
<213> ORGANISM: Homo sapiens

<400> SEQUENCE: 86

Gly Gly Gly Lys Ala His His Leu
1               5

<210> SEQ ID NO 87
<211> LENGTH: 8
<212> TYPE: PRT
<213> ORGANISM: Homo sapiens

<400> SEQUENCE: 87

Gly Ser Asn Thr Glu Lys His Leu
1               5

<210> SEQ ID NO 88
<211> LENGTH: 8
<212> TYPE: PRT
<213> ORGANISM: Homo sapiens

<400> SEQUENCE: 88

Gly Pro Ala His Gln Asp Arg Leu
1               5

<210> SEQ ID NO 89
<211> LENGTH: 8
<212> TYPE: PRT
<213> ORGANISM: Homo sapiens

<400> SEQUENCE: 89

Gly His Glu Gln Lys Gly His Leu
1               5

<210> SEQ ID NO 90
<211> LENGTH: 8
<212> TYPE: PRT
<213> ORGANISM: Homo sapiens

<400> SEQUENCE: 90

Gly Pro Ala His Gln Asp His Leu
1               5

<210> SEQ ID NO 91
```

```
<211> LENGTH: 8
<212> TYPE: PRT
<213> ORGANISM: Homo sapiens

<400> SEQUENCE: 91

Gly Ser Tyr Pro Ser Ser His Leu
 1               5

<210> SEQ ID NO 92
<211> LENGTH: 8
<212> TYPE: PRT
<213> ORGANISM: Homo sapiens

<400> SEQUENCE: 92

Gly Ser Gln Asn Gln Val His Leu
 1               5

<210> SEQ ID NO 93
<211> LENGTH: 8
<212> TYPE: PRT
<213> ORGANISM: Homo sapiens

<400> SEQUENCE: 93

Gly His Ala Gln Lys Arg Arg Leu
 1               5

<210> SEQ ID NO 94
<211> LENGTH: 7
<212> TYPE: PRT
<213> ORGANISM: Homo sapiens

<400> SEQUENCE: 94

Gly Gly Lys Ser Arg Arg Leu
 1               5

<210> SEQ ID NO 95
<211> LENGTH: 8
<212> TYPE: PRT
<213> ORGANISM: Homo sapiens

<400> SEQUENCE: 95

Gly His Glu Ala Lys Arg Arg Leu
 1               5

<210> SEQ ID NO 96
<211> LENGTH: 7
<212> TYPE: PRT
<213> ORGANISM: Homo sapiens

<400> SEQUENCE: 96

Gly Gly Gln Lys Arg Arg Leu
 1               5

<210> SEQ ID NO 97
<211> LENGTH: 8
<212> TYPE: PRT
<213> ORGANISM: Homo sapiens

<400> SEQUENCE: 97

Gly His Glu Gln Lys Arg Arg Ala
 1               5

<210> SEQ ID NO 98
<211> LENGTH: 7
<212> TYPE: PRT
```

<213> ORGANISM: Homo sapiens

<400> SEQUENCE: 98

Gly Gly Ala Lys Arg Arg Leu
1               5

<210> SEQ ID NO 99
<211> LENGTH: 8
<212> TYPE: PRT
<213> ORGANISM: Homo sapiens

<400> SEQUENCE: 99

Gly His Glu Gln Lys Arg Arg Ser
1               5

<210> SEQ ID NO 100
<211> LENGTH: 7
<212> TYPE: PRT
<213> ORGANISM: Homo sapiens

<400> SEQUENCE: 100

Gly Gly Lys Lys Arg Arg Leu
1               5

<210> SEQ ID NO 101
<211> LENGTH: 7
<212> TYPE: PRT
<213> ORGANISM: Homo sapiens

<400> SEQUENCE: 101

Gly Gly His Lys Arg Arg Leu
1               5

<210> SEQ ID NO 102
<211> LENGTH: 7
<212> TYPE: PRT
<213> ORGANISM: Homo sapiens

<400> SEQUENCE: 102

Gly Gly Lys Ala Phe Arg Leu
1               5

<210> SEQ ID NO 103
<211> LENGTH: 8
<212> TYPE: PRT
<213> ORGANISM: Homo sapiens

<400> SEQUENCE: 103

Gly Ala Glu Gln Lys Arg Arg Leu
1               5

<210> SEQ ID NO 104
<211> LENGTH: 7
<212> TYPE: PRT
<213> ORGANISM: Homo sapiens

<400> SEQUENCE: 104

Gly Gly Lys Ala Gln Arg Leu
1               5

<210> SEQ ID NO 105
<211> LENGTH: 7
<212> TYPE: PRT
<213> ORGANISM: Homo sapiens -continued

```
<400> SEQUENCE: 105

Gly Gly Lys Ala Arg Arg Leu
 1               5

<210> SEQ ID NO 106
<211> LENGTH: 7
<212> TYPE: PRT
<213> ORGANISM: Homo sapiens

<400> SEQUENCE: 106

Gly Gly Lys Gln Arg Arg Leu
 1               5

<210> SEQ ID NO 107
<211> LENGTH: 7
<212> TYPE: PRT
<213> ORGANISM: Homo sapiens

<400> SEQUENCE: 107

Gly Gly Lys His Arg Arg Leu
 1               5

<210> SEQ ID NO 108
<211> LENGTH: 8
<212> TYPE: PRT
<213> ORGANISM: Homo sapiens

<400> SEQUENCE: 108

Gly His Glu Gln Ala Arg Arg Leu
 1               5

<210> SEQ ID NO 109
<211> LENGTH: 7
<212> TYPE: PRT
<213> ORGANISM: Homo sapiens

<400> SEQUENCE: 109

Gly Gly Lys Ala Lys Arg Leu
 1               5

<210> SEQ ID NO 110
<211> LENGTH: 8
<212> TYPE: PRT
<213> ORGANISM: Homo sapiens
<220> FEATURE:
<221> NAME/KEY: VARIANT
<222> LOCATION: 8
<223> OTHER INFORMATION: Xaa = dL which is an isomer of Leu

<400> SEQUENCE: 110

Gly His Glu Gln Lys Arg Arg Xaa
 1               5

<210> SEQ ID NO 111
<211> LENGTH: 7
<212> TYPE: PRT
<213> ORGANISM: Homo sapiens

<400> SEQUENCE: 111

Gly Gly Lys Ala Arg Arg Ser
 1               5

<210> SEQ ID NO 112
<211> LENGTH: 7
<212> TYPE: PRT
```

<213> ORGANISM: Homo sapiens

<400> SEQUENCE: 112

Gly Gly Lys Ala Arg Lys Leu
1               5

<210> SEQ ID NO 113
<211> LENGTH: 8
<212> TYPE: PRT
<213> ORGANISM: Homo sapiens

<400> SEQUENCE: 113

Gly His Glu Gln Lys Arg Arg Glu
1               5

<210> SEQ ID NO 114
<211> LENGTH: 7
<212> TYPE: PRT
<213> ORGANISM: Homo sapiens

<400> SEQUENCE: 114

Gly Gly Lys Ala His Arg Leu
1               5

<210> SEQ ID NO 115
<211> LENGTH: 7
<212> TYPE: PRT
<213> ORGANISM: Homo sapiens

<400> SEQUENCE: 115

Gly Gly Lys Ala Asn Arg Leu
1               5

<210> SEQ ID NO 116
<211> LENGTH: 7
<212> TYPE: PRT
<213> ORGANISM: Homo sapiens

<400> SEQUENCE: 116

Gly Gly Lys Ala Arg Gln Leu
1               5

<210> SEQ ID NO 117
<211> LENGTH: 7
<212> TYPE: PRT
<213> ORGANISM: Homo sapiens

<400> SEQUENCE: 117

Gly Gly Lys Ala Arg His Leu
1               5

<210> SEQ ID NO 118
<211> LENGTH: 7
<212> TYPE: PRT
<213> ORGANISM: Homo sapiens

<400> SEQUENCE: 118

Gly Gly Lys Ala Arg Asn Leu
1               5

<210> SEQ ID NO 119
<211> LENGTH: 7
<212> TYPE: PRT
<213> ORGANISM: Homo sapiens
<220> FEATURE:

```
<221> NAME/KEY: VARIANT
<222> LOCATION: 5
<223> OTHER INFORMATION: Xaa = dR which is an isomer of Arg

<400> SEQUENCE: 119

Gly Gly Lys Ala Xaa Arg Leu
 1               5

<210> SEQ ID NO 120
<211> LENGTH: 7
<212> TYPE: PRT
<213> ORGANISM: Homo sapiens

<400> SEQUENCE: 120

Gly Gly Lys Ala Lys Lys Leu
 1               5

<210> SEQ ID NO 121
<211> LENGTH: 7
<212> TYPE: PRT
<213> ORGANISM: Homo sapiens

<400> SEQUENCE: 121

Gly Gly Lys Ala His Lys Leu
 1               5

<210> SEQ ID NO 122
<211> LENGTH: 7
<212> TYPE: PRT
<213> ORGANISM: Homo sapiens
<220> FEATURE:
<221> NAME/KEY: VARIANT
<222> LOCATION: 6
<223> OTHER INFORMATION: Xaa = dR which is an isomer of Arg

<400> SEQUENCE: 122

Gly Gly Lys Ala Arg Xaa Leu
 1               5

<210> SEQ ID NO 123
<211> LENGTH: 7
<212> TYPE: PRT
<213> ORGANISM: Homo sapiens
<220> FEATURE:
<221> NAME/KEY: VARIANT
<222> LOCATION: 5, 6
<223> OTHER INFORMATION: Xaa = dR which is an isomer of Arg

<400> SEQUENCE: 123

Gly Gly Lys Ala Xaa Xaa Leu
 1               5

<210> SEQ ID NO 124
<211> LENGTH: 5
<212> TYPE: PRT
<213> ORGANISM: Homo sapiens

<400> SEQUENCE: 124

Ala Gln Lys Arg Arg
 1               5

<210> SEQ ID NO 125
<211> LENGTH: 5
<212> TYPE: PRT
<213> ORGANISM: Homo sapiens

<400> SEQUENCE: 125
```

Gly Lys Ser Arg Arg
1               5

<210> SEQ ID NO 126
<211> LENGTH: 5
<212> TYPE: PRT
<213> ORGANISM: Homo sapiens

<400> SEQUENCE: 126

Glu Gln Lys Arg Arg
1               5

<210> SEQ ID NO 127
<211> LENGTH: 5
<212> TYPE: PRT
<213> ORGANISM: Homo sapiens

<400> SEQUENCE: 127

Glu Ala Lys Arg Arg
1               5

<210> SEQ ID NO 128
<211> LENGTH: 5
<212> TYPE: PRT
<213> ORGANISM: Homo sapiens

<400> SEQUENCE: 128

Gly Gln Lys Arg Arg
1               5

<210> SEQ ID NO 129
<211> LENGTH: 5
<212> TYPE: PRT
<213> ORGANISM: Homo sapiens

<400> SEQUENCE: 129

Gly Ala Lys Arg Arg
1               5

<210> SEQ ID NO 130
<211> LENGTH: 5
<212> TYPE: PRT
<213> ORGANISM: Homo sapiens

<400> SEQUENCE: 130

Gly Lys Lys Arg Arg
1               5

<210> SEQ ID NO 131
<211> LENGTH: 5
<212> TYPE: PRT
<213> ORGANISM: Homo sapiens

<400> SEQUENCE: 131

Gly His Lys Arg Arg
1               5

<210> SEQ ID NO 132
<211> LENGTH: 5
<212> TYPE: PRT
<213> ORGANISM: Homo sapiens

<400> SEQUENCE: 132

Gly Lys Ala Phe Arg

```
<210> SEQ ID NO 133
<211> LENGTH: 5
<212> TYPE: PRT
<213> ORGANISM: Homo sapiens

<400> SEQUENCE: 133

Glu Lys Ala Gln Arg
 1               5

<210> SEQ ID NO 134
<211> LENGTH: 5
<212> TYPE: PRT
<213> ORGANISM: Homo sapiens

<400> SEQUENCE: 134

Glu Lys Ala Arg Arg
 1               5

<210> SEQ ID NO 135
<211> LENGTH: 7
<212> TYPE: PRT
<213> ORGANISM: Homo sapiens

<400> SEQUENCE: 135

Gly Gly Lys Ala Arg Arg Leu
 1               5
```

ACTIVATION OF PEPTIDE PRODRUGS BY HK2

This application claims benefit under 35 U.S.C. 119(e) to a provisional application 60/146,316 filed Jul. 29, 1999.

FIELD OF THE INVENTION

This invention relates generally to the targeted activation of biologically active materials to cells that produce human glandular kallikrein (hK2) and more specifically to hK2-specific peptides substrates that can act as drug carriers. In addition it relates to prodrugs consisting of a peptide covalently coupled to a cytotoxic drug such that the peptide-drug bond can be hydrolyzed by hK-2. The coupling of the peptide to the cytotoxic drug creates an inactive prodrug that can only become activated at sites where enzymatically active hK-2 is being produced.

BACKGROUND OF THE INVENTION

There is currently no effective therapy for men with metastatic prostate cancer who relapse after androgen ablation, even though numerous agents have been tested over the past thirty years. Prolonged administration of effective concentrations of standard chemotherapeutic agents is usually not possible because of dose-limiting systemic toxicities.

Human Glandular Kallikrein 2 (hK2) is the protein product of the human kallikrein gene hKLK2, one of three related kallikrein genes that also include hKLK1 and hKLK3. These three genes are clustered on chromosome 19q13.2–q13.4. The protein product of hKLK3 is prostate-specific antigen (PSA). While PSA is the predominant tissue kallikrein in the prostate, hK2 is also found almost exclusively in the prostate. hK2 is a glycoprotein containing 237 amino acids and a mass of 28.5 kDa. hK2 and PSA share some properties such as high amino acid sequence identity, prostate localization, androgen regulation and gene expression, but are quite distinct form one another biochemically.

hK2 and PSA differ most markedly in their enzyme properties. Unlike PSA, a chymotrypsin-like protease, hK2 displays the trypsin-like specificity common to most members of the kallikrein family of proteases. hK2 can cleave semenogelin proteins, with an activity that is comparable to PSA. The level of hK2 in the seminal fluid is only 1% of the level of PSA. hK2 has trypsin-like activity, similar to hK1, although it does not appear to function as a classic kininogenase.

In the normal prostate, the levels of expressed hK2 protein are lower than those of PSA. However, hK2 is more highly expressed by prostate cancer cells than by normal prostate epithelium. Comparison of immunohistochemical staining patterns demonstrated incrementally increased staining in poorly differentiated prostate cancers. The intensity of staining has been found to increase with increasing Gleason score, in contrast to PSA, which tends to show decreased staining with increasing Gleason grade, suggesting that hK2 might potentially be a better tumor marker for prostate cancer than PSA.

Recently, three independent groups reported that recombinant hK2 could convert inactive pro-PSA in to the mature PSA protease by release of the propeptide in vitro, thus establishing a possible physiologic connection between hK2 and PSA. hK2 is also secreted in an inactive precursor form. Pro-hK2 may have autocatalytic activity, but the mechanism of activation in vivo is unknown and may involve several additional enzymes. hK2 has also been shown to activate single chain urokinase-type plasminogen activator, scuPA, to the active two-chain form, uPA, which is highly correlated with prostate cancer metastasis. More recently, hK2 has been shown to inactivate the major tissue inhibitor of uPA, plasminogen activator inhibitor-1 (PAI-1). Thus hK2 may influence the progression of prostate cancer by the activation of uPA and by the inactivation of PAI-1.

Enzymatically active hK2 has also been shown to form covalent complexes in vitro with plasma protease inhibitors such as $\alpha_1$-antichymotrypsin (ACT), $\alpha_2$-antiplasmin, antithrombin III, protein C inhibitor (PCI), and $\alpha_2$-macroglobulin (AMG). hK2 has been identified in prostate cancer serum in a complex with ACT.

Thapsigargin (TG) is a sesquiterpene-γ-lactone available by extraction from the seeds and roots of the umbelliferous plant *Thapsia garganica L*. Thapsigargin selectively inhibits the sarcoplasmic reticulum (SR) and endoplasmic reticulum (ER) $Ca^{2+}$-ATPase (SERCA) pump, found in skeletal, cardiac, muscle and brain microsomes. The apparent dissociation constant for TG from the SERCA pump is 2.2 pM or less.

SUMMARY OF THE INVENTION

The present invention provides a novel class of oligopeptides that include amino acid sequences containing cleavage sites for human glandular kallikrein (HK2)(see FIG. 1). These cleavage sites are derived from an hK2 specific cleavage map of semenogelin I and II, (see FIG. 1). These oligo-peptides are useful in assays that can determine the free hK2 protease activity. Furthermore, the invention also provides a therapeutic prodrug composition, comprising a therapeutic drug linked to a peptide, which is specifically cleaved by hK2. The linkage substantially inhibits the non-specific toxicity of the drug, and cleavage of the peptide releases the drug, activating it or restoring its non-specific toxicity.

The invention also provides a method for treating cell proliferative disorders, including those which involve the production of hK2, in subjects having or at risk of having such disorders. The method involves administering to the subject a therapeutically effective amount of the composition of the invention.

The invention also provides a method of producing the prodrug composition of the invention. In another embodiment, the invention provides a method of detecting hK2 activity in tissue. In yet another embodiment, the invention provides a method of selecting appropriate prodrugs for use in treating cell proliferative disorders involving hK2-production.

The invention also provides a method for detecting a cell proliferative disorder associated with hK2 production in a tissue of a subject, comprising contacting a target cellular component suspected of having a hK2 associated disorder, with a reagent which detects enzymatically active hK2.

The invention also provides a method of determining hK2 activity in a hK2-containing sample, comprising contacting the sample with a detectably labeled peptide which is specifically cleaved by hK2 for a period of time sufficient to allow hK2 to cleave the peptide, detecting the detectable label to yield a detection level, which is then compared to the detection level obtained by contacting the same detectably labeled peptide with a standard hK2 sample of known activity.

The invention also provides a method of imaging soft tissue and/or bone metastases which produce hK2, comprising administering a lipophilic-imaging label linked to a peptide which is specifically cleaved by hK2 to a patient suspected of having a hK2-associated cell proliferative disorder, allowing hK2 to cleave the peptide, allowing the lipophilic imaging label to accumulate in the tissue and/or bone, allowing the subject to clear the uncleaved peptide, and imaging the subject for diagnostic purposes.

Unless otherwise defined, all technical and scientific terms used herein have the ordinary meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other reference materials mentioned herein are incorporated by reference in their entirety. In case of conflict, the present specification, including definitions, will control. In addition the materials, methods, and examples are illustrative only and not intended to be limiting.

BRIEF DESCRIPTION OF THE FIGURE

FIG. 1 is a portion of the amino acid sequence of Semenogelin I (SEQ ID NOs:1–4) and Semenogelin II (SEQ ID NOs:5–11), showing the cleavage sites for human kallikrein 2.

DETAILED DESCRIPTION

The invention provides a novel class of peptides that contain a cleavage site specific for human glandular kallikrein 2 (hK2). These peptides are efficiently and specifically cleaved by hK2. These peptides are useful for substantially inhibiting the non-specific toxicity of the therapeutic agents prior to the agents contracting a tissue containing hK2. Thus, the invention includes prodrugs which include peptides linked to therapeutic agents. The prodrugs of the invention comprise peptide sequences containing a cleavage site specific for hK2 and therapeutic drugs. The compositions do not show significant non-specific toxicity, but in environments where hK2 is found, the composition becomes activated when peptide is cleaved, releasing the therapeutic drug, which regains its non-specific toxicity.

hK2 Specific Peptide

As used herein the term "human glandular kallikrein 2" (hK2) means human glandular kallikrein 2, as well as other proteases that have the same or substantially the same proteolytic cleavage specificity as hK2. As used herein, the term "naturally occurring amino acid side chain" refers to the side chains of amino acids known in the art as occurring in proteins, including those produced by post translational modifications of amino acid side chains. The term "contacting" refers to exposing tissue to the peptides, therapeutic drugs or prodrugs of the invention so that they can effectively inhibit cellular processes, or kill cells. Contacting may be in vitro, for example by adding the peptide, drug or prodrug to a tissue culture to test for susceptibility of the tissue to the peptide, drug or prodrug. Contacting may be in vivo, for example administering the peptide, drug, or prodrug to a subject with a cell proliferative disorder, such as prostate or breast cancer. By "polypeptide" is meant any chain of amino acids, regardless of length or post-translational modification (e.g., glycosylation or phosphorylation). As written herein, amino acid sequences are presented according to the standard convention, namely that the amino-terminus of the peptide is on the left, and the carboxy terminus on the right. In one aspect the invention features a peptide containing an amino acid sequence that includes a cleavage site specific for hk2 or an enzyme having a proteolytic activity of hK2. The peptides of the invention are preferably not more than 20 amino acids in length, more preferably to more than ten amino acids in length. The preferred amino acid sequences of the invention are linear. In an embodiment of the invention the amino acid sequence may be cyclical such that the cyclical form of the sequence is an inactive drug that can become an activated drug upon cleavage by hK2 and linearization.

The cleavage site recognized by hK2 is flanked by at least an amino acid sequence, $X_4X_3X_2X_1$. This oligopeptide contains the amino acid arginine, histidine or lysine at position $X_1$. $X_2$ can be arginine, phenylalanine, lysine, or histidine. $X_3$ can be lysine, serine, alanine, histidine or glutamine. $X_4$ can be from 0 to 20 further amino acids, preferably at least two further amino acids. Some preferred embodiments include a sequence for $X_4$ that is substantially identical to the 20 amino acids in the wild type semenogelin I or semenogelin II sequence that are the from fourth to twenty fourth amino acids to the N-terminal side of recognized semenogelin cleavage sites. The amino acid sequence can further comprise $X_{-1}$, which is linked to the carboxy terminus of $X_1$ to create the amino acid sequence $X_4X_3X_2X_1X_{-1}$. $X_{-1}$ is up to a further 10 amino acids, and can include any amino acids. Preferably $X_1$ has leucine, alanine or serine linked to the carboxy terminus of $X_1$. $X_{-1}$ can include L- or D-amino acids. The hK2 cleavage site is located at the carboxy terminal side of $X_1$.

In some preferred peptides, both $X_1$ and $X_2$ are arginine.

Some examples of preferred peptides include (Note that the symbol [] denotes an hK2 cleavage site):
1. Lys-Arg-Arg][(SEQ ID NO:12)
2. Ser-Arg-Arg][(SEQ ID NO:13)
3. Ala-Arg-Arg][(SEQ ID NO:14)
4. His-Arg-Arg][(SEQ ID NO:15)
5. Gln-Arg-Arg][(SEQ ID NO:16)
6. Ala-Phe-Arg][(SEQ ID NO:17)
7. Ala-Gln-Arg][(SEQ ID NO:18)
8. Ala-Lys-Arg][(SEQ ID NO:19)
9. Ala-Arg-Lys][(SEQ ID NO:20)
10. Ala-His-Arg][(SEQ ID NO:21)

Additional preferred peptides of longer sequence length include:
11. Gln-Lys-Arg-Arg][(SEQ ID NO:22)
12. Lys-Ser-Arg-Arg][(SEQ ID NO:23)
13. Ala-Lys-Arg-Arg][(SEQ ID NO:24)
14. Lys-Lys-Arg-Arg][(SEQ ID NO:25)
15. His-Lys-Arg-Arg][(SEQ ID NO:26)
16. Lys-Ala-Phe-Arg][(SEQ ID NO:27)
17. Lys-Ala-Gln-Arg][(SEQ ID NO:28)
18. Lys-Ala-Lys-Arg][(SEQ ID NO:29)
19. Lys-Ala-Arg-Lys][(SEQ ID NO:30)
20. Lys-Ala-His-Arg][(SEQ ID NO:31)

Additional preferred peptides that include an X–1 amino acid are:
21. Lys-Arg-Arg][Leu (SEQ ID NO:32)
22. Ser-Arg-Arg][Leu (SEQ ID NO:33)
23. Ala-Arg-Arg][Leu (SEQ ID NO:34)
24. Ala-Arg-Arg][Ser (SEQ ID NO:35)
25. His-Arg-Arg][Ala (SEQ ID NO:36)
26. Gln-Arg-Arg][Leu (SEQ ID NO:37)
27. Ala-Phe-Arg][Leu (SEQ ID NO:38)
28. Ala-Gln-Arg][Leu (SEQ ID NO:39)
29. Ala-Lys-Arg][Leu (SEQ ID NO:40)

30. Ala-Arg-Lys][Leu (SEQ ID NO:41)
31. Ala-His-Arg][Leu (SEQ ID NO:42)

Preferred peptides of still longer sequence length having $X_{-1}$ include:

32. His-Ala-Gln-Lys-Arg-Arg][Leu (SEQ ID NO:43)
33. Gly-Gly-Lys-Ser-Arg-Arg][Leu (SEQ ID NO:44)
34. His-Glu-Gln-Lys-Arg-Arg][Leu (SEQ ID NO:45)
35. His-Glu-Ala-Lys-Arg-Arg][Leu (SEQ ID NO:46)
36. Gly-Gly-Gln-Lys-Arg-Arg][Leu (SEQ ID NO:47)
37. His-Glu-Gln-Lys-Arg-Arg][Ala (SEQ ID NO:48)
38. Gly-Gly-Ala-Lys-Arg-Arg][Leu (SEQ ID NO:49)
39. His-Glu-Gln-Lys-Arg-Arg][Ser (SEQ ID NO:50
40. Gly-Gly-Lys-Lys-Arg-Arg][Leu (SEQ ID NO:51)
41. Gly-Gly-His-Lys-Arg-Arg][Leu (SEQ ID NO:52)

Other embodiments of peptide sequences which are useful for cleavage by hK2 and proteases with the hydrolytic activity of hK2 are disclosed in the Examples section. Further examples of the peptides of the invention are constructed as analogs of, derivatives of and conservative variations on the amino acids sequences disclosed herein. Thus, the broader group of peptides having hydrophilic and hydrophobic substitutions, and conservative variations are encompassed by the invention. Those of skill in the art can make similar substitutions to achieve peptides with greater activity and or specificity toward hK2. For example, the invention includes peptide sequences described above, as well as analogs or derivatives thereof, as long as the bioactivity of the peptide remains. Minor modifications of the primary amino acid sequence of the peptides of the invention may result in peptides that have substantially equivalent activity as compared to the specific peptides described herein. Such modifications may be deliberate, as by site directed mutagenesis or chemical synthesis, or may be spontaneous. All of the peptides produced by these modifications are included herein, as long as the biological activity of the original peptide remains, i.e. susceptibility to cleavage by hK2.

Further, deletion of one or more amino acids can also result in a modification of the structure of the resultant molecule without significantly altering its biological activity. This can lead to the development of a smaller active molecule without significantly altering its biological activity. This can lead to the development of a smaller active molecule which would also have utility. For example, amino or carboxy-terminal amino acids which may not be required for biological activity of the particular peptide can be removed. Peptides of the invention include any analog, homolog, mutant or isomer or derivative of the peptides disclosed in the present invention, as long as bioactivity described herein remains. All peptides described have sequences comprised of L-amino acids; however, D-forms of the amino acids can be synthetically produced and used in the peptides described herein.

The peptides of the invention include peptides which are conservative variations of those peptides specifically exemplified herein. The term "conservative variation" as used herein denotes the replacement of an amino acid residue by another, biologically similar residue. Examples of conserved variations include the substitution of one hydrophobic residue such as isoleucine, valine, leucine, alanine, cysteine, glycine, phenylalanine, proline, tryptophan, tyrosine, norleucine or methionine for another or the substitution of one polar residue for another such as the substitution of arginine for lysine or histidine, glutamic for aspartic acids or glutamine for asparagine, and the like. Neutral hydrophilic amino acids that can be substituted for one another include asparagine, glutamine, serine, and threonine. Such conservative substitutions are within the definitions of the classes of peptides of the invention with respect to X positions which may be any number of amino acids. The peptides that are produced by such conservative variation can be screened for suitability of use in the prodrugs of the invention according to the methods for selecting prodrugs provided herein.

A wide variety of groups can be linked to the carboxy terminus of $X_1$ or $X_{-1}$. Notably, therapeutic drugs can be linked to this position. In this way advantage is taken of the hK2 specificity of the cleavage site, as well as other functional characteristics of the peptides of the invention. Preferably, the therapeutic drugs are linked to the carboxy terminus of $X_1$ either directly or through a linker group. The direct linkage is preferably through an amide bond, in order to utilize the proteolytic activity and specificity of hK2. If the connection between the therapeutic drug and the amino acid sequence is made through a linker, this connection is also preferably made through an amide bond, for the same reason. This linker may be connected to the therapeutic drug through any of the bond types and chemical groups known to those skilled in the art. The linker may consist of the amino acid (s) comprising $X_{-1}$. The linker may remain on the therapeutic drug, or may be removed soon thereafter, either by further reactions or in a self-cleaving step. Self-cleaving linkers are those linkers which can intramolecularly cyclize and release the drug or undergo spontaneous $S_N1$ solvolysis and release the drug upon peptide cleavage.

Other materials such as detectable labels or imaging compounds can be linked to the peptide. Groups can be linked to the amino terminus of $X_7$, including such moieties as antibodies, and peptide toxins, including the 26 amino acid toxin, melittin and the 35 amino acid toxin cecropin B for example. Both of these peptide toxins have shown toxicity against cancer cell lines. The N-terminal amino acid of the peptide may also be attached to the C-terminal amino acid either via an amide bond formed by the N-terminal amine and the C-terminal carboxyl, or via coupling of side chains on the N-terminal and C-terminal amino acids or via disulfide bond formed when the N-terminal and C-terminal amino acids both consist of the amino acid cysteine. Further, it is envisioned that the peptides described herein can be coupled, via the carboxy terminus of $X_1$ or $X_{-1}$, to a variety of peptide toxins (for example, melittin and cecropin are examples of insect toxins), so that cleavage by hK2 liberates an active toxin. Additionally, the peptide could be coupled to a protein such that the protein is connected at the $X_1$ or $X_{-1}$ amino acid of the peptide. This coupling can be used to create an inactive proenzyme so that cleavage by a tissue-specific protease (such as hK2 or PSA) would cause a conformational change in the protein to activate it. For example, Pseudomonas toxin has a leader peptide sequence which must be cleaved to activate the protein. Additionally, the peptide sequence could be used to couple a drug to an antibody. The antibody could be coupled to the N-terminus of the peptide sequence (that is, $X_4$ or higher X amino acids), and the drug coupled to the carboxy terminus (that is $X_1$ or $X_{-1}$). The antibody would bind to a cell surface protein and tissue-specific protease present in the extracellular fluid could cleave the drug from the peptide linker.

The preferred amino acid sequence can be constructed to be highly specific for cleavage by hK2. In addition the peptide sequence can be constructed to be highly selective towards cleavage by hK2 as compared to purified extracellular and intracellular proteases. Highly-specific hK2 sequences can also be constructed that are also stable toward cleavage in human sera.

The peptides of the invention can be synthesized according to any of the recognized procedures in the art, including such commonly used methods as t-boc or fmoc protection of alpha-amino groups. Both methods involve stepwise syntheses whereby a single amino acid is added at each step starting from the C-terminus of the peptide. Peptides of the invention can also be synthesized by well-known solid phase peptide synthesis methods. Peptides can be characterized using standard techniques such as amino acid analysis, thin layer chromatography, or high performance liquid chromatography, for example.

The invention encompasses isolated nucleic acid molecules encoding the hK2- specific peptides of the invention, vectors containing these nucleic acid molecules, cells harboring recombinant DNA encoding the hK2-specific peptides of the invention, and fusion proteins that include the hK2 specific peptides of the invention. Especially preferred are nucleic acid molecules encoding the polypeptides described herein.

Prodrug Compositions

The invention also features prodrug compositions that consist of a therapeutic drug linked to a peptide containing a cleavage site that is specific for hK2 or any enzyme that has the enzymatic activity of hK2. As noted above, the peptides of the invention can be used to target therapeutic drugs for activation within hK2 producing tissue. The peptides that are useful in the prodrugs of the invention are those described above.

The therapeutic drugs that may be used in the prodrugs of the invention include any drug which can be directly or indirectly linked to the hK2-specifically cleavable peptides of the invention. Preferred drugs are those containing a primary amine. The presence of the primary amine allows for formation of an amide bond between the drug and the peptide and this bond serves as the cleavage site for hK2. The primary amines may be found in the drugs as commonly provided, or they may be added to the drugs by chemical synthesis.

Certain therapeutic drugs contain primary amines and are among the preferred agents. These include the anthracycline family of drugs, the vinca drugs, the mitomycins, the bleomycins, the cytotoxic nucleosides, the pteridine family of drugs, diynenes, the podophyllotoxins, and the taxanes. Particularly useful members of these classes include, for example, doxorubicin, daunorubicin, carminomycin, idarubicin, epirubicin, aminopterin, methotrexate, methopterin, mitomycin C porfiromycin, 5-flurouracil, cytosine arabinoside, etoposide, melphalan, vincristine, vinblastine, vindesine, 6-mercaptopurine, and the like.

Other therapeutic drugs are required to have primary amines introduced by chemical or biochemical synthesis, for example sesquiterpene-lactones such as thapsigargin, and thapsigargin and many others know to those skilled in the art. The thapsigargins are a group of natural products isolated from species of the umbelliferous genus *Thapsia*. The term thapsigargins has been defined by Christensen, et al., *Prog. Chem. Nat. Prod.*, 71(1997) 130–165. These derivatives contain a means of linking the therapeutic drug to carrier moieties, including peptides and antibodies. The peptides and antibodies can include those which specifically interact with antigens including hK2. The interactions can involve cleavage of the peptide to release the therapeutic analogs of sesquiterpene-γ-lactones. Particular therapeutic analogs or sesquiterpene-γ-lactones, such as thapsigargins, are disclosed in U.S. patent application Ser. No. 09/588,822, filed Jun. 7, 2000, entitled "Tissue Specific Prodrug," and U.S. patent application Ser. No. 09/588,921, filed Jun. 7, 2000, entitled "Tissue Specific Prodrug," both of which are incorporated herein in their entireties.

For example, thapsigargins with alkanoyl, alkenoyl, and arenoyl groups at carbon 8 or carbon 2, can be employed in the practice of the invention disclosed herein. Groups such as $CO-(CH=CH)_{n1}-(CH_2)_{n2}-A-NH_2$, $CO-(CH_2)_{n2}-(CH=CH)_{n1}-Ar-NH_2$, $CO-(CH_2)_{n2}-(CH=CH)_{n1}-CO-NH-Ar-NH_2$ and $CO-(CH=CH)_{n1}-(CH_2)_{n2}-CO-NH-Ar-NH_2$ and substituted variations thereof can be used as carbon 8 substituents, where n1 and n2 are from 0 to 5, and Ar is any substituted or unsubstituted aryl group. Substituents which may be present on Ar include short and medium chain alkyl, alkanoxy, aryl, aryloxy, and alkenoxy groups, nitro, halo, and primary secondary or tertiary amino groups, as well as such groups connected to Ar by ester amide linkages. In other embodiments of thapsigargin analogs, these substituents groups are represented by unsubstituted, or alkyl-, aryl-, halo-, alkoxy-, alkenyl-, amido-, or amino-substituted $CO-(CH_2)_{n3}-NH_2$, where n3 is from 0 to 15, preferably 3–15, and also preferably 6–12. Particularly preferred substituent groups within this class are 6-aminohexanoyl, 7-aminoheptanoyl, 8-aminooctanoyl, 9-aminononanoyl, 10-aminodecanoyl, 11-aminoundecanoyl, and 12-aminododecanoyl. These substituents are generally synthesized from the corresponding amino acids, 6-aminohexanoic acid, and so forth. The amino acids are N-terminal protected by standard methods, for example Boc protection. Dicyclohexylcarbodiimide (DCCI)-promoted coupling of the N-terminal protected substituent to thapsigargin, followed by standard deprotection reactions produces primary amine-containing thapsigargin analogs.

The substituents can also carry primary amines in the form of an amino amide group attached to the alkanoyl-, alkenoyl-, or arenoyl substituents. For example, C-terminal protection of a first amino acid such as 6-aminohexanoic acid and the like, by standard C-terminal protection techniques such as methyl ester formation by treatment with methanol and thionyl chloride, can be followed by coupling the N-terminal of the first amino acid with an N-protected second amino acid of any type.

The peptide and therapeutic drug are linked directly or indirectly (by a linker) through the carboxy terminus of the amino acid at $X_1$ or $X_{-1}$. The site of attachment on the therapeutic drug must be such that, when coupled to the peptide, the non-specific toxicity of the drug is substantially inhibited. Thus the prodrugs should not be significantly toxic.

The prodrugs of the invention may also comprise groups which provide solubility to the prodrug as a whole in the solvent in which the prodrug is to be used. Most often the solvent is water. This feature of the invention is important in the event that neither the peptide nor the therapeutic drug is soluble enough to provide overall solubility to the prodrug. These groups include polysaccharides or other polyhydroxylated moieties. For example, dextran, cyclodextrin, starch and derivatives of such groups may be included in the prodrug of the invention.

Thapsigargin Analogs

The invention also features derivatized thapsigargin analogs with the derivatization including providing the molecule with a residue substituted with a primary amine. The primary amine can be used to link the derivatized thapsigargin analog with various other moieties. Among these are peptides which link to the analog to give prodrugs without significant non-specific toxicity, but enzymatic reaction with hK2 affords the toxic drug. These enzymatic reactions can liberate the non-specific toxic thapsigargin derivative, for example by cleavage through proteolysis or hydrolysis, various reactions of the side chains of the eptide, or other reactions which restore the non-specific toxicity of the thapsigargin analog. These reactions can serve to activate the derivatized thapsigargin analog locally at hK2 producing tissue, and with relative exclusivity to regions in which these enzymatic reactions take place. The primary amine containing thapsigargin analog can also be linked to an antibody, oligonucleotide, or polypeptide which binds to an epitope or receptor in the target tissue.

Thapsigargin is a sesquiterpene-γ-lactone having the structure disclosed in International Publication No. WO 98/52966. Primary amines can be placed in substituent groups pendant from either C-2 or C-8 carbon (carbons are numbered as described in International Publication No. WO 98/52966). Preferred primary amine containing thapsigargin analogs that can be coupled to the peptides described above include those described previously by the inventors ("Tissue Specific Prodrug" International Patent Application PCT/US98/10285, published as International Publication No. WO 98/52966, corresponding to U.S. Ser. No. 60/047,070 and 60/080,046, filed May 15, 1997 and Mar. 30, 1998). These primary amine-containing analogs have non-specific toxicity toward cells. This toxicity is measured as the toxicity needed to kill 50% of clonogenic cells ($LC_{50}$). The $LC_{50}$ of the analogs of this invention is desirably at most 10 μM, preferably at most 2 μM and more preferably at most 200 nM of analog.

Methods of Treatment Using Prodrugs

The invention also provides methods of treatment of treating hK2-producing cell proliferative disorders of the invention with the prodrugs of the invention. The prodrugs of the invention and/or analogs or derivatives thereof can be administered to any host, including a human or non-human animal, in an amount effective to treat a disorder.

The prodrugs of the invention can be administered parenterally by injection or by gradual infusion over time. The prodrugs can be administered intravenously, intraperitoneally, intramuscularly, subcutaneously, intracavity, or transdermally. Preferred methods for delivery of the prodrug include intravenous or subcutaneous administration. Other methods of administration will be known to those skilled in the art.

Method of Producing Prodrugs

The invention provides a method of producing the prodrugs of the invention. This method involves linking a therapeutically active drug to a peptide of the invention described above. In certain embodiments the peptide is linked directly to the drug; in other embodiments the peptide is indirectly linked to the drug via a linker. In each case the carboxy terminus of the peptide is used for linking. That is, in an amino acid sequence $X_5X_4X_3X_2X_1$, the link is established through $X_1$. If $X_{-1}$ is linked to the carboxy terminus of $X_1$, the carboxy terminus of $X_{-1}$ is used for linking. The therapeutic drug contains a primary amine to facilitate the formation of an amide bond with the peptide. Many acceptable methods for coupling carboxyl and amino groups to form amide bonds are know to those skilled in the art.

The peptide may be coupled to the therapeutic drug via a linker. Suitable linkers include any chemical group which contains a primary amine and include amino acids, primary amine-containing alkyl, alkenyl or arenyl groups. The connection between the linker and the therapeutic drug may be of any type know in the art, preferably covalent bonding.

In certain embodiments, the linker comprises an amino acid or amino acid sequence. The sequence may be of any length, but is preferably between 1 and 10 amino acids, most preferably between 1 and 5 amino acids. Preferred amino acids are leucine or an amino acid sequence containing this amino acid, especially at their amino termini.

Method of Screening Tissue and Determining hK2 Activity

In another aspect the invention provides a method of detecting hK2-producing tissue using peptides of the invention, as described above. The method is carried out by contacting a detectably labeled peptide of the invention with target tissue for a period of time sufficient to allow hK2 to cleave the peptide and release the detectable label. The detectable label is then detected. The level of detection is compared to that of a control sample not contacted with the target tissue. Many varieties of detectable labels are available, including optically based labels such as chromophoric, chemiluminescent, fluoresecent or phosphorescent labels and radioactive labels, such as alpha, beta, or gamma emitting labels. In addition a peptide label consisting of an amino acid sequence comprising $X_{-1}$ can be utilized for detection such that release of the $X_{-1}$ label by hK2 proteolysis can be detected by high pressure liquid chromatography. The peptide sequences of the invention can also be incorporated into the protein sequence of a fluorescent protein such that cleavage of the incorporated hK2 specific sequence by hK2 results in either an increased or decreased fluorescent signal that can be measured using the appropriate fluorometric measuring instrument.

The invention provides a method for detecting a cell proliferative disorder that comprises contacting an hK2-specific peptide with a cell suspected of producing hK2. The hK2 reactive peptide is labeled by a compound so that cleavage by hK2 can be detected. For purposes of the invention, a peptide specific for hK2 may be used to detect the level of enzymatically active hK2 in biological tissues such as saliva, blood, urine, and tissue culture media. In an embodiment of the method a specific hK2 inhibitor is used to confirm that the activity being measured is solely due to peptide cleavage by hK2 and not secondary to non-specific cleavage by other proteases present in the biological tissue being assayed. Examples of hK2 inhibitors that can be employed in the method include the addition of zinc ions, or the addition of hK2 specific antibodies that bind to the catalytic site of hK2 thereby inhibiting enzymatic activity of hK2.

Method of Screening Prodrugs

The invention also provides a method of selecting potential prodrugs for use in the invention. The method generally consists of contacting prodrugs of the invention with hK2-producing tissue and non-hK2 producing tissue in a parallel experiment. The prodrugs which exert toxic effects in the presence of hK2-producing tissue, but not in the presence of non-hK2 producing tissue are suitable for the uses of the invention.

The invention will be further described in the following examples, which do not limit the scope of the invention described in the claims.

EXAMPLES

Example 1

Production of Recombinant hK2

Recombinant hK2 was produced and purified as described in Lövgren et al., *Biochem. Bioph. Res. Co.*, 238, 549–555 (1997). Semenogelin 1 and 11 were isolated from human semen as described previously in Malm et al, *Eur. J. Biochem.*, 238, 48–53 (1996). The tripeptide aminomethyl-coumarin (AMC) substrates Boc-Phe-Ser-Arg-AMC (SEQ ID NO:53), Boc-Gln-Gly-Arg-AMC (SEQ ID NO:54), H-Pro-Phe-Arg-AMC (SEQ ID NO:55), boc-Val-Pro-Arg-AMC (SEQ ID NO:56), H-D-Val-Leu-Lys-AMC (SEQ ID NO:57), Tos-Gly-Pro-Arg-AMC-(SEQ ID NO:58), Tos-Gly-Pro-Lys-AMC (SEQ ID NO:59), Z-Leu-Leu-Arg-AMC (SEQ ID NO:60), Z-Val-Val-Arg-AMC (SEQ ID NO:61), Z-Ala-Arg-Arg-AMC (SEQ ID NO:62), and H-Arg-Gln-Arg-Arg-AMC (SEQ ID NO:63) were from Bachem (Bubendorf, Switzerland). The heptapeptide substrates Mu-Ala-Pro-Val-Leu-Ile-Leu-Ser-Arg-AMC (SEQ ID NO:64) and Mu-Val-Pro-Leu-Ile-Gln-Ser-Arg-AMC (SEQ ID NO:65) corresponding to the pro peptides of PSA hK2 were from Enzyme Systems Product (Livermore, Calif., USA). ACT was purified from human blood plasma as described in Christenssson et al., *Eur. J. Biochem.*, 194, 755–63 (1990). PCI was provided by Prof. Johan Stenflo (Malmö University Hospital, Malmö, Sweden), and SLPI, and PSTI by Prof. Kjell Ohlsson (Malmo University Hospital, Malmo, Sweden). Benzamidine hydrochloride was from Amresco® (Solon, Ohio, USA), leupeptin and antipain were from ICN Biomedicals (Costa Mesa, Calif., USA), Aprotinin was from Sigma (St. Louis, Mo., USA), and PPACK from Calbiochem (La Jolla, Calif., USA).

Example 2

Determination of hK2 Cleavage Sites in Semenogelin I and II

Purified semenogelin 1 and 11 (40 µg), was incubated with hK2 (8 µg) in 50 mM Tris pH 7.5, 0.1 M NaCl, 0.15 M urea at 37° C. for 4 hours. The fragments generated were purified by reverse phase HPLC using a C-8 column. Elution was achieved with a 0–30% (0.25%/min.) linear acetonitrile gradient and fractions corresponding to individual peaks were collected. The amino terminal sequences of the individual peaks were determined by automated amino terminal sequencing with an Applied Biosystems 470 A gas-phase sequencer. Cleavage of either Sg I or Sg II with hK2 results in generation of a multitude of peptides. After partial separation of the peptides by reversed phase HPLC on a C-8 column we obtained sequences of four cleavage sites in Sg I and seven cleavage sites in Sg II. The semenogelins contain three types of internal repeats, as described in Lilja et al., *J. Biol. Chem.*, 264, 1894–2000 (1989) and Lilja et al., *PNAS USA*, 89, 4559–63 (1992). Most of the identified hK2 cleavage sites were located in different positions in these repeats. The position and sequence of the cleavage sites in Sg I and Sg II are shown in FIG. 1, where the cleavage sites are aligned underneath the arrows. Three identical sites of cleavage in repeat type I, which occurs twice in SgI and four times in SgII, were identified at positions 274 and 334 in Sg I and position 454 in Sg II. All but one of the cleavage sites contained arginine at positon P1, except for one of the cleavages in Semenogelin II, which occurred on the carboxy terminal side of a histidine. It is noteworthy that no cleavages occurred on the carboxy terminal side of a lysine. Five of the eleven cleavage sites determined were double basic, the amino acid at P2 being either arginine, lysine or histidine, indicating that hK2 may cleave substrates at both mono- and di-basic sites. In one case P2 was occupied by phenylalanine which is found in the same position in PCI. In addition glycine, valine, serine, glutamine and aspartate were found at P2. In most cleavage sites P3 was occupied by a large group; in six of the cleavages it was glutamine or glutamate and in the other serine, histidine or lysine. In one case alanine was found at P3. When looking at common motifs if can be seen that in seven cases serine was found in P6. Basic amino acids were found in addition to positions P1 and P2 once in P5, twice in P3, P4, P6 and P8, and four times in P7. On the carboxy terminal side of the cleavage site leucine was found five times in P-1 and tyrosine four times in position P-3.

Example 3 pH Dependence of the Enzymatic Action of hK2

The pH dependence of hK2 was determined using a universal buffer composed of 29 mM citric acid, 29 mM citric acid, 29 mM $KH_2PO_4$, 29 mM boric acid 0.1 M NaCl and 0.2% bovine serum albumin (BSA). The buffering range is Ph 2.4–11.8. The rate of the cleavage of the substrate I-1295 (100 µM) by 1.6 pmol hK2 was followed for 20 minutes at pH 5, 5.5, 6, 6.5, 7, 7.5, 8, 8.5, 9, 9.5, and 10.

Example 4

Determination of Kinetic Constants

The measurements were done with Fluoroscan II (Labsystems, Helsinki, Finland) using a 355 nm excitation filter and a 460 m emission filter. The fluorescence of 7-amino-4-methylcoumarin (AMC) (Sigma, St. Louis, Mo., USA) was determined to be 700 FIU/nmol and this value was used in the calculations of the rate of product formation. Unless otherwise indicated all final analyses were performed in 200 µl of the buffer 50 mM Tris pH 7.5, 0.1 M NaCl, and 0.2% BSA at 37° C. using 1.6 pmol hK2. BSA was added to the reaction mixture in order to minimize adsorption of the enzyme to the walls of the microtiter wells. The amount of hK2 was quantified by a commercial PSA immunoassay (Prostatus, Wallac, Turku, Finland) with the Mabs H1 17 and H50 which recognize PSA and hK2 equally well (Lövgren et al., *Biochem. Biophys. Res. Co.*, 213, 888–895 (1995)). Under the conditions described, 1.6 pmol of the hK2 preparation cleaved 50 pmol/min of the 100 µM substrate Pro-Phe-Arg-AMC. During the 20 minute measurement time the consumption of the substrates is <7% of their total amount and was not considered to affect the reaction rate. Initial analyses of the substrates were performed with 3.2 pmol hK2 at a substrate concentration of 250 µM. The $K_m$ value for the substrates cleaved by hK2 at these conditions were determined using at least four substrate concentrations ranging from $0.2 \times K_m$ to $5 \times K_m$. The $K_m$ and kcat values were calculated from Lineweaver-Burk plots.

Substrates ending in either arginine or lysine were tested. The kinetic constants for hydrolysis of the substrates by hK2 are shown in Table 1. The best substrate was the kallikrein substrate Pro-Phe-Arg-AMC (SEQ ID NO:55) having the highest $k_{cat}$ and $k_{cat}/K_m$ values. The cathepsin B substrate Ala-Arg-Arg-AMC (SEQ ID NO:62) was also cleaved quite effectively having a relatively high $k_{cat}$ value and a low $K_m$ resulting in a four times lower $k_{cat}/K_m$ value than that obtained for the kallidrein substrate Pro Phe-Arg-AMC (SEQ ID NO:55). However, no

TABLE 1

Substrate Hydrolysis by hK2

| Substrates | Km (M) | Kcat (min$^{-1}$) | Kcat/km ($\mu$M$^{-1}$min$^{-1}$) | Activity (%) |
|---|---|---|---|---|
| Pro Phe Arg-AMC (SEQ ID NO:55) | 40 | 55 | 1.375 | 100 |
| Val Pro Arg-AMC (SEQ ID NO:56) | 48 | 1.6 | 0.034 | 6 |
| Gly Pro Arg-AMC (SEQ ID NO:58) | | NR | | |
| Gly Pro Lys-AMC (SEQ ID NO:59) | | NR | | |
| Leu Leu Arg-AMC (SEQ ID NO:60) | 71 | 2.4 | 0.034 | 7 |
| Val Val Arg-AMC (SEQ ID NO:61) | | NR | | |
| Val Leu Lys-AMC (SEQ ID NO:57) | | NR | | |
| Phe Ser Arg-AMC (SEQ ID NO:53) | | NR | | |
| Gln Gly Arg-AMC (SEQ ID NO:54) | | NR | | |
| Ala Arg Arg-AMC (SEQ ID NO:62) | 20 | 7.2 | 0.360 | 33 |
| Arg Gln Arg Arg-AMC (SEQ ID NO:63) | | NR | | |

The activity listed in Table 1 is the hydrolytic activity of hK2 with 100 μM substrate in relation to the hydrolytic activity of hK2 with 100 μM of the tissue kallikrein substrate H-Pro-Phe-Arg-AMC (SEQ ID NO:55). The entry "N.R." means that no reaction was detected.

Example 5

Inhibition of hK2

Activity of hK2 (1.6 pmol) was monitored using the substrate H-Pro-Phe-Arg-AMC (SEQ ID NO:55) (90 μM). Inhibitors, at commonly used concentrations, and hK2 (8.3 nM) were mixed and proteolysis of 90 μM H-Pro-Phe-Arg-AMC (SEQ ID NO:55) was followed up to 20 minutes, starting directly or 10 minutes after mixing the enzyme with various inhibitors. Inhibition was evaluated by comparison with enzyme-free controls.

The effects of several protease inhibitors on the hydrolytic activity of hK2 are shown in Table 2. The proteolytic activity is expressed in percentage of inhibitor-free control after 10 minutes of incubation.

TABLE 2

Effects of Protease Inhibitors on hK2 Activity

| Inhibitor | Final concentration (μM) | Activity (%) |
|---|---|---|
| ZnCl$_2$ | 200 | 1.2 |
| | 100 | 10 |
| PCI | 0.08 | 0 |
| | 0.016 | 50 |
| PPACK | 5 | 0 |
| Benzamidine | 20,000 | 8 |
| | 5000 | 27 |
| Leupeptin | 100 | 12 |
| Antipain | 500 | 10 |
| | 100 | 33 |
| Aprotinin | 5 | 75 |
| | 30 | 47 |
| SLPI | 4 | 35 |
| | 0.08 | 92 |
| PSTI | 4 | 89 |
| | 0.08 | 100 |
| ACT | 0.8 | 100 |

None of the reversible protease inhibitors fully inhibited 8 nM hK2 when 90 μM substrate was used. HK2 was only weakly inhibited by the reversible peptide inhibitors leupeptin and antipain. The highest recommended working concentration (100 μM) of the respective inhibitor was found to give approximately 60% and 90% inhibition of hK2 activity against the 90 μM peptide substrate. Aprotinin proved not to be good hK2 inhibitor and benzamidine is required at concentrations above 20 mM for efficient inhibition. The irreversible thrombin inhibitor PPACK inhibited hK2 rapidly when used at a 5 μM concentration. Therefore, PPACK can be used to obtain fast irreversible inhibition of hK2. ZnCl$_2$ effectively inhibits hK2 but when used at high concentrations, easily causes precipitation of proteins. Of the protease inhibitors present in the prostate, PSTI and SLPI inhibited hK2 weakly and this inhibition is probably not physiologically significant. This reaction is however slow and no inhibition of the hK2 activity by a 100-fold molar excess of ACT was detected during the 20 minute measurement time.

Example 6

Kinetic Analysis of hK2 Inhibition by Zinc

The inhibition of hK2 by Zn$^{2+}$ was studied using the substrates Pro-Phe-Arg-AMC (SEQ ID NO:55) and Ala-Arg-Arg-AMC (SEQ ID NO:62) at concentrations varying from 9 to 180 μM and ZcCl$_2$ concentrations ranging from 0.5 μM to 1 mM. Since BSA contains several binding sites for Zn$^{2+}$ it could not be used in the kinetics buffer during the zinc inhibition experiments. The binding of hK2 to the microtiter well walls caused a constant decrease in the reaction rate, which was however similar to all zinc concentrations. The velocities were calculated from a five-minute measurement time after mixing of the enzyme with the buffer containing substrate and zinc.

The enzymatic activity of hK2 was inhibited by zinc ions at micromolar concentrations, and the inhibition was totally reversed by addition of EDTA. The inhibition of hK2 by zinc was first tested against competitive, uncompetitive, mixed, non-competitive, and partial non-competitive inhibitor models using commonly used formulas described for the respective inhibition models. Zn$^{2+}$ both increased the K$_m$ and decreased the V$_{max}$. The Dixon plots ([Zn$^{2+}$]/v) for the inhibition were not linear. However, at low zinc ion concentrations the inhibition pattern looked competitive. The inhibition mechanism is clearly more complex than the ones described by the formulas used. Further analysis of the inhibition mechanism was done by deriving the rate equations for various more complex mechanisms and analyzing the data by least-squares best-fit systems. The possible mechanism required two bound zinc ions, and is presented by Scheme 1. In the best mechanism, the first bound zinc ion does not cause inhibition (k=k', or k' was even slightly higher than k).

Scheme 1

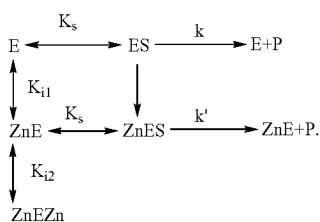

For this mechanism, the rate of product formation (v) will be given by the following equation:

$$v = \frac{S}{Ks}\left(k + k'\frac{Zn}{Kil}\right)e$$

where the concentration of free enzyme e is the total enzyme concentration divided by the sum of a) {(the zinc concentration divided by $K_{i1}$) times (the zinc concentration divided by $K_{i2}$)} and b) {(the zinc concentration divided by $K_{i1}$) plus 1} times {(the substrate concentration divided by $K_s$) plus 1}.

The equation fitted the experimental data quite satisfactorily. The constant values were $K_{i1}$=4.6±3.9 μM, $K_{i2}$=3.2±0.7 μM, and k=k'. Best fit analyses were accomplished also for mechanisms involving inactivating dimerizations of the hK2 molecules as zinc ions have been shown to inhibit the mouse gamma-NGF and to be critical in the association of the mouse 7S NGF complex (Pattison et al., *Biochemistry*, 14, 2733–39 (1975)). These mechanisms did not result in a more optimal fit than those in Scheme 2.

Example 7

Kinetic Analysis of hK2 Inhibition by PCI

The progress of the reaction of hK2 (8nM final concentration) with the substrate Pro-Phe-Arg-AMC (SEQ ID NO:55) was monitored at two different substrate concentrations without or with different concentrations of PCI (80, 40 or 16 nM final concentration). The fluorescence measurements were started directly after mixing the enzyme with the inhibitor. The inhibitor of hK2 by PCI could be described by the slow-binding inhibition mechanism presented in Scheme 2, which has been used in analyzing the interaction of PCI with various serine proteases (Hermans et al., *Biochem. J*, 295, 239–245 (1993), and Hermans et al., *Biochemistry*, 33, 5440–44 (1994)). This mechanism assumes that a reversible complex is formed between the proteinase and seine proteinase inhibitor (serpin). The issues justifying the use of the slow binding inhibition mechanism despite the commonly held view that the seprin-proteinase complex is irreversible has been discussed in more detail by Hermans et al. (1993.

Scheme 2

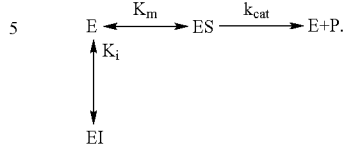

where E, S, P, and I represent the enzyme, substrate (peptidyl AMC), product (AMC), product (AMC) and inhibitor (PCI) respectively; $K_m$ and $k_{cat}$ are Michaelis and catalytic constants for the enzyme substrate interaction, and $K_i$ is the inhibition constant which is equal to $k_{diss}/K_{ass}$, $K_{ass}$ and $K_{diss}$ are the association and dissociation rate constants for the enzyme inhibitor complex. For this mechanism, the progress curve of product formation is given by:

$$P = v_s t + \frac{v_o - v_s}{k'}(1 - e^{-kt})$$

where P is the amount of product at time t, k' is an apparent first order rate constant, and $v_o$ and $v_s$ are the initial and steady-state velocities respectively. For the mechanism shown in Scheme 2, $v_o$ will be independent of the inhibitor concentration, and $v_s$ and k' will vary with the inhibitor concentration according to the following equations:

$$v_s = \frac{v_o}{1 + I/K_i'}$$

$$k' = k_{diss} + k'_{ass} \cdot I$$
$$= k'_{ass}(K_i' + I)$$

where $K'_i$ and $k'_{ass}$ are apparent constants that are related to the true constants by the expressions:

$$K_i = K_i'/(1 + S/K_m)$$
$$k_{ass} = k'_{ass}(1 + S/K_m)$$

The effect of heparin of the association rate of hK2 and PCI was studied using 40 nM PCI, 8 nM hK2, and heparin concentrations ranging from $10^{-4}$ to $10^{-7}$ M. The effect of the heparin on hK2 activity was analysed by determining $K_m$ and $k_{cat}$ for the substrate at different heparin concentrations. Heparin slightly increased the $K_m$ of the substrate (data not shown). The increase had no significant effect on the calculation of the constants.

Example 8

Hydrolysis of hK2 Substrates

Hydrolyses of particular hK2 substrates were carried out at a hK2 concentrations of 1 μg/ml in 50 mM Tris buffer, with 0.1 M NaCl, at pH 7.8. Serum hydrolysis measurements were carried out in 50% fresh human serum in 50 mM Tris buffer, with 0.1 M NaCl, at pH 7.8. The single letter amino acid code was used to designate the peptide sequences used for Table 4. The units FU are arbitrary fluorescence units. The entries "U.D." were for measurements of less than 0.01 FU/hour.

TABLE 4

Hydrolysis of hK2 Substrates

| Peptide Sequence | | | | | | | | hK2 Hydrolysis Rate (FU/hr/mg) | Serum Hydrolysis Rate FU/hr |
|---|---|---|---|---|---|---|---|---|---|
| P7 | P6 | P5 | P4 | P3 | P2 | P1 | P'1 | | |
| G | H | E | Q | K | R | R | L (SEQ ID NO: 66) | 5966.31 | 0.17 |
| G | G | G | K | A | R | R | L (SEQ ID NO: 67) | 4784.22 | 0.03 |
| G | G | G | K | A | H | R | L (SEQ ID NO: 68) | 4100.94 | 0.09 |
| G | P | A | H | Q | R | R | L (SEQ ID NO: 69) | 4017.81 | 0.10 |
| G | S | K | G | H | F | R | L (SEQ ID NO: 70) | 3029.27 | 0.04 |
| G | S | K | G | H | R | R | L (SEQ ID NO: 71) | 2649.96 | UD |
| G | K | D | V | S | R | R | L (SEQ ID NO: 72) | 2316.12 | 0.08 |
| G | S | Q | N | Q | R | R | L (SEQ ID NO: 73) | 2100.48 | 0.05 |
| G | S | Y | P | S | R | R | L (SEQ ID NO: 74) | 2060.21 | 0.09 |
| G | S | Y | P | S | S | R | L (SEQ ID NO: 75) | 1456.18 | 0.06 |
| G | H | E | Q | K | G | R | L (SEQ ID NO: 76) | 650.80 | 0.04 |
| G | S | N | T | E | R | R | L (SEQ ID NO: 77) | 592.34 | UD |
| G | S | Y | E | E | R | R | L (SEQ ID NO: 78) | 324.75 | 0.04 |
| G | K | D | V | S | G | R | L (SEQ ID NO: 79) | 242.91 | 0.05 |
| G | S | N | T | E | K | R | L (SEQ ID NO: 80) | 255.90 | 0.13 |
| G | S | K | G | H | F | H | L (SEQ ID NO: 81) | 171.47 | 0.10 |
| G | S | Q | N | Q | V | R | L (SEQ ID NO: 82) | 193.55 | 0.03 |
| G | P | L | I | L | S | R | L (SEQ ID NO: 83) | 118.21 | 0.07 |
| G | S | Y | E | E | R | H | L (SEQ ID NO: 84) | 42.87 | 0.09 |
| G | K | D | V | S | G | H | L (SEQ ID NO: 85) | 67.55 | 0.05 |
| G | G | G | K | A | H | H | L (SEQ ID NO: 86) | 70.15 | 0.05 |
| G | S | N | T | E | K | H | L (SEQ ID NO: 87) | 80.54 | 0.03 |
| G | P | A | H | Q | D | R | L (SEQ ID NO: 88) | 75.34 | 0.06 |
| G | H | E | Q | K | G | H | L (SEQ ID NO: 89) | 1.30 | UD |
| G | P | A | H | Q | D | H | L (SEQ ID NO: 90) | 48.06 | 0.00 |
| G | S | Y | P | S | S | H | L (SEQ ID NO: 91) | 24.68 | UD |
| G | S | Q | N | Q | V | H | L (SEQ ID NO: 92) | 32.48 | 0.03 |

TABLE 5

Additional hK2 Substrates

| Substrate Sequence | | | | | | | | hK2 Hydrolysis Rate (FU/hr/mg) | Serum Hydrolysis Rate FU/hr |
|---|---|---|---|---|---|---|---|---|---|
| P7 | P6 | P5 | P4 | P3 | P2 | P1 | P'1 | | |
| G | H | A | Q | K | R | R | L (SEQ ID NO: 93) | 3665.1 | 0.08 |
|   | G | G | K | S | R | R | L (SEQ ID NO: 94) | 3439.7 | 0.03 |
| G | H | E | Q | K | R | R | L (SEQ ID NO: 66) | 3366.5 | UD |
| G | H | E | A | K | R | R | L (SEQ ID NO: 95) | 3324.1 | UD |
|   | G | G | Q | K | R | R | L (SEQ ID NO: 96) | 3267.4 | 0.02 |
| G | H | E | Q | K | R | R | A (SEQ ID NO: 97) | 3051.5 | 0.06 |
|   | G | G | A | K | R | R | L (SEQ ID NO: 98) | 2773.0 | 0.02 |
| G | H | E | Q | K | R | R | S (SEQ ID NO: 99) | 2638.5 | UD |
|   | G | G | K | K | R | R | L (SEQ ID NO: 100) | 2583.0 | UD |
|   | G | G | H | K | R | R | L (SEQ ID NO: 101) | 2428.4 | UD |
|   | G | G | K | A | F | R | L (SEQ ID ND: 102) | 2374.2 | 0.07 |
| G | A | E | Q | K | R | R | L (SEQ ID NO: 103) | 2325.8 | 0.10 |
|   | G | G | K | A | Q | R | L (SEQ ID NO: 104) | 2233.7 | 0.04 |
|   | G | G | K | A | R | R | L (SEQ ID NO: 105) | 2171.2 | UD |
|   | G | G | K | Q | R | R | L (SEQ ID NO: 106) | 2171.2 | 0.02 |
|   | G | G | K | H | R | R | L (SEQ ID NO: 107) | 2079.2 | UD |
| G | H | E | Q | A | R | R | L (SEQ ID NO: 108) | 1956.4 | 0.14 |
|   | G | G | K | A | K | R | L (SEQ ID NO: 109) | 1788.9 | 0.14 |
| G | H | E | Q | K | R | R | dL (SEQ ID NO: 110) | 1690.9 | 0.15 |
|   | G | G | K | A | R | R | S (SEQ ID NO: 111) | 1609.5 | UD |
|   | G | G | K | A | R | K | L (SEQ ID NO: 112) | 1602.4 | UD |
| G | H | E | Q | K | R | R | E (SEO ID NO: 113) | 1473.8 | UD |
|   | G | G | K | A | H | R | L (SEQ ID NO: 114) | 1287.4 | 0.10 |
|   | G | G | K | A | N | R | L (SEQ ID NO: 115) | 1113.9 | 0.01 |
|   | G | G | K | A | R | Q | L (SEQ ID NO: 116) | 1021.9 | 0.13 |
|   | G | G | K | A | R | H | L (SEQ ID NO: 117) | 939.3 | UD |
|   | G | G | K | A | R | N | L (SEQ ID NO: 118) | 828.4 | 0.25 |
|   | G | G | K | A | dR | R | L (SEQ ID NO: 119) | 494.4 | 0.06 |
|   | G | G | K | A | K | K | L (SEQ ID NO: 120) | 77.9 | UD |
|   | G | G | K | A | H | K | L (SEQ ID NO: 121) | 73.2 | UD |
|   | G | G | K | A | R | dR | L (SEQ ID NO: 122) | 49.6 | UD |
|   | G | G | K | A | dR | dR | L (SEQ ID NO: 123) | 16.5 | UD |

It is to be understood that while the invention has been described in conjunction with the detailed description thereof, the forgoing description is intended to illustrate and not limit the scope of the invention, which is defined by the scope of the appended claims. Other aspects, advantages, and modifications are within the scope of the following claims.

What is claimed is:

1. A composition comprising a prodrug, the prodrug comprising
   a therapeutically active drug; and
   a peptide comprising an amino acid sequence having a cleavage site
   specific for an enzyme having a proteolytic activity of human kallikrein 2 (hK2),
   wherein the peptide has 20 or fewer amino acids in length,
   wherein the peptide has linked to the therapeutically active drug to inhibit the therapeutic activity of the drug, and wherein the therapeutically active drug is cleaved from the peptide upon proteolysis by an enzyme having a proteolytic activity of human kallikrein 2 (hK2).

2. The composition of claim 1, wherein the peptide is linked directly to the therapeutic drug.

3. The composition of claim 2, wherein the peptide is linked directly to a primary amine group on the drug.

4. The composition of claim 1, wherein the peptide is linked to the therapeutic drug via a linker.

5. The composition of claim 4, wherein the therapeutic drug is a compound belonging to the group of thapsigargins which have been derivatized with a moiety containing a primary amine group, the peptide is Gly-Gly-Lys-Ala-Arg-Arg-Leu (SEQ ID NO:135), and the linker is selected from the group consisting of:
   (a) CO—(CH=CH)$_{n1}$—(CH$_2$)$_{n2}$—Ar—NH$_2$,
   (b) CO—(CH$_2$)$_{n2}$—(CH=CH)$_{n1}$—Ar—NH$_2$,
   (c) CO—(CH$_2$)$_{n2}$—(CH=CH)$_{n1}$—CO—NH—Ar—NH$_2$,
   (d) CO—(CH=CH)$_{n1}$—(CH$_2$)$_{n2}$—CO—NH—Ar—NH$_2$,
   (e) CO—(CH$_2$)$_{n3}$—NH$_2$, and
   (f) (CO—(CH$_2$)$_{n3}$—NH—CO—CH(R$_4$)—NH$_2$,
   each of which is unsubstituted or alkyl-, aryl-, halo-, alkoxy-, alkenyl-, amido- or amino-substituted, and wherein n1 and n2 are from 0 to 5, n3 is from 0 to 15, Ar is any substituted or unsubstituted aryl group, attachment of NH$_2$ to Ar is in a ortho, meta or para position with respect to the remainder of the linker, and R$_4$ is any naturally occurring amino acid side chain.

6. The composition of claim 4, wherein the linker is an amino acid sequence.

7. The composition of claim 6, wherein the linker comprises a leucine residue.

8. The composition of claim 1, wherein the therapeutically active drug inhibits a sarcoplasmic reticulum and endoplasmic reticulum Ca$^{2+}$-ATPase (SERCA) pump.

9. The composition of claim 8, wherein the therapeutically active drug is selected from the group of primary amine containing thapsigargins and thapsigargin derivatives.

10. The composition of claim 1, wherein the therapeutically active drug intercalates into a polynucleotide.

11. The composition of claim 10, wherein the therapeutically active drug is an anthracycline antibiotic.

12. The composition of claim 11, wherein the therapeutically active drug is selected from the group consisting of doxorubicin, daunorubicin, epirubicin and idarubicin.

13. The composition of claim 1, wherein the peptide is Gly-Gly-Lys-Ala-Arg-Arg-Leu (SEQ ID NO:135).

14. The composition of claim 1, wherein the therapeutically active drug has an LC$_{50}$ toward ER Ca$^{2+}$-ATPase of at most 500 nM.

15. The composition of claim 14, wherein the therapeutically active drug has an L$_{50}$ toward ER Ca$^{2+}$-ATPase of at most 50 nM.

16. The composition of claim 1, wherein the therapeutically active drug has an $LC_{50}$ toward hK2-producing tissue of at most 20 μM.

17. The composition of claim 16, wherein the therapeutically active drug has an $LC_{50}$ toward hK2-producing tissue of less than or equal to 2.0 μM.

18. The composition of claim 1, further comprising an added substituent which renders the composition water soluble.

19. The composition of claim 18, wherein the added substituent is a polysaccharide.

20. The composition of claim 19, wherein the polysaccharide is selected from the group consisting of modified or unmodified dextran, cyclodextrin and starch.

21. A method of producing a prodrug, the method comprising the step of linking
a therapeutically active drug and
a peptide comprising an amino acid sequence having a cleavage site specific for an enzyme having a proteolytic activity of human kallikrein 2 (hK2), wherein the peptide is 20 or fewer amino acids in length,
wherein linking of the peptide to the drug inhibits the therapeutic activity of the drug.

22. The method of claim 21, wherein the therapeutically active drug has a primary amine.

23. The method of claim 21, wherein the prodrug contains a linker between the peptide and the drug.

24. The method of claim 23, wherein the linker is an amino acid sequence which comprises leucine.

25. The method of claim 21, wherein the peptide further comprises a capping group attached to the N-terminus of the peptide, the capping group inhibiting endopeptidase activity on the peptide.

26. The method of claim 25, wherein the capping group is selected from the group consisting of acetyl, morpholinocarbonyl, benzyloxycarbonyl, glutaryl, and succinyl substituents.

27. A method of treating a cell proliferative disorder which produces hK2, the method comprising administering the composition of claim 1 in a therapeutically effective amount to a subject having the cell proliferative disorder.

28. The method of claim 27, wherein the disorder is benign.

29. The method of claim 27, wherein the disorder is malignant.

30. The method of claim 29, wherein the malignant disorder is prostate cancer.

31. The method of claim 29, wherein the malignant disorder is breast cancer.

32. A method of detecting human kallikrein 2-producing tissue, the method comprising:
contacting the tissue with a composition comprising
a detectably labeled peptide for a period of time sufficient to allow cleavage of the peptide, where the peptide comprises an amino acid sequence having a cleavage site specific for an enzyme having a proteolytic activity of human kallikrein 2 (hK2), wherein the peptide has 20 or fewer amino acids in length, and wherein the peptide comprises a detectable label; and
detecting the detectable label.

33. The method of claim 32, wherein the peptide further comprises a capping group attached to the N-terminus of the peptide, the group inhibiting endopeptidase activity.

34. The method of claim 33, wherein the capping group is selected from the group consisting of acetyl, morpholinocarbonyl, benzyloxycarbonyl, glutaryl, and succinyl substituents.

35. The method of claim 32, wherein the detectable label is a fluorescent label.

36. The method of claim 35, wherein the fluorescent label is selected from the group consisting of 7-amino-4-methyl coumarin, 7-amino-4-trifluoromethyl coumarin, rhodamine 110, and 6-aminoquinoline.

37. The method of claim 32, wherein the detectable label is a radioactive label.

38. The method of claim 37, wherein the radioactive label is selected from the group consisting of tritium, carbon-14, and iodine-125.

39. The method of claim 32, wherein the detectable label is a chromophoric label.

40. The method of claim 32, wherein the detectable label is a chemiluminescent label.

* * * * *